United States Patent
Aihara et al.

(10) Patent No.: US 10,886,017 B2
(45) Date of Patent: Jan. 5, 2021

(54) ANALYSIS SYSTEM AND ANALYSIS METHOD

(71) Applicant: Hitachi, Ltd., Tokyo (JP)

(72) Inventors: Shimpei Aihara, Tokyo (JP); Takeshi Tanaka, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 434 days.

(21) Appl. No.: 15/073,925

(22) Filed: Mar. 18, 2016

(65) Prior Publication Data

US 2016/0363607 A1 Dec. 15, 2016

(30) Foreign Application Priority Data

Jun. 11, 2015 (JP) .................................. 2015-118347

(51) Int. Cl.
  *G01P 3/68* (2006.01)
  *G16H 20/30* (2018.01)
  (Continued)

(52) U.S. Cl.
  CPC ........... *G16H 20/30* (2018.01); *A61B 5/0022* (2013.01); *A61B 5/015* (2013.01); *A61B 5/1113* (2013.01);
  (Continued)

(58) Field of Classification Search
  CPC ..... A61B 5/6801; A61B 5/1113; A61B 5/015; A61B 5/0022; G01P 3/36; G01P 3/68;
  (Continued)

(56) References Cited

U.S. PATENT DOCUMENTS

2007/0213126 A1* 9/2007 Deutsch ............. A63B 69/0053
  463/36
2009/0256688 A1 10/2009 Khan
  (Continued)

FOREIGN PATENT DOCUMENTS

JP 10-276351 A 10/1998
WO WO 2010/065886 A1 6/2010
  (Continued)

OTHER PUBLICATIONS

Extended European Search Report issued in counterpart European Application No. 16159372.8 dated Nov. 2, 2016 (Ten (10) pages).

*Primary Examiner* — Brigitte A Paterson
(74) *Attorney, Agent, or Firm* — Crowell & Moring LLP

(57) ABSTRACT

An analysis system includes a storage module for storing a track indicating in time series a position of an individual that is moving as track data and for storing sensor data indicating in time series a measurement result of the individual by a sensor worn by the individual, a speed calculation module for calculating a speed index indicating a movement speed of the individual based on the track data, an index calculation module for calculating a behavior index indicating a movement intensity of the individual based on the sensor data, a similarity degree calculation module for calculating a degree of similarity between the speed index and the behavior index based on changes in time series of the speed index and the behavior index, and an association module for associating the track and the individual on which the sensor data has been measured based on the degree of similarity.

14 Claims, 26 Drawing Sheets

(51) Int. Cl.
  *A61B 5/00*  (2006.01)
  *A61B 5/01*  (2006.01)
  *A61B 5/11*  (2006.01)
  *G01S 19/19*  (2010.01)
  *G01S 17/87*  (2020.01)
  *G01P 3/36*  (2006.01)

(52) U.S. Cl.
  CPC .............. *A61B 5/6801* (2013.01); *G01P 3/36* (2013.01); *G01P 3/68* (2013.01); *G01S 17/87* (2013.01); *G01S 19/19* (2013.01)

(58) Field of Classification Search
  CPC .... G01S 17/87; G01S 19/19; G06F 17/30781; G06F 19/3481; G06Q 10/0639
  See application file for complete search history.

(56) References Cited

U.S. PATENT DOCUMENTS

| | | |
|---|---|---|
| 2010/0283630 A1 | 11/2010 | Alonso |
| 2012/0084053 A1* | 4/2012 | Yuen .................... A61B 5/0002 |
| | | 702/160 |
| 2012/0253484 A1 | 10/2012 | Burich et al. |
| 2014/0167973 A1* | 6/2014 | Letchner ............... A61B 5/1118 |
| | | 340/870.02 |
| 2016/0158598 A1* | 6/2016 | Dolezel .................. A63B 53/04 |
| | | 473/223 |

FOREIGN PATENT DOCUMENTS

| | | |
|---|---|---|
| WO | WO 2015/069123 A1 | 5/2015 |
| WO | WO 2015/081303 A1 | 6/2015 |

\* cited by examiner

TRACK INFORMATION — 21

| TABLE NAME | AREA TABLE |
|---|---|

201

| No. | LOGIC NAME |
|---|---|
| 1 | AREA ID — 2011 |
| 2 | AREA NAME — 2012 |
| 3 | AREA APEX COORDINATES — 2013 |

| TABLE NAME | TRACK LINE TABLE |
|---|---|

202

| No. | LOGIC NAME |
|---|---|
| 1 | TRACK ID — 2021 |
| 2 | START TIME POINT — 2022 |
| 3 | FINISH TIME POINT — 2023 |
| 4 | TRACK COORDINATES ROW — 2024 |

| TABLE NAME | TRACK INFORMATION TABLE |
|---|---|

203

| No. | LOGIC NAME |
|---|---|
| 1 | TRACK ID — 2031 |
| 2 | MEASUREMENT DATE AND TIME — 2032 |
| 3 | x COORDINATE — 2033 |
| 4 | y COORDINATE — 2034 |
| 5 | AREA ID — 2035 |

*FIG. 3*

|       | 232 | | | | | | TRACK ID | 23 |

| MEASUREMENT DATE AND TIME | d00001 | d00002 | d00003 | d00004 | d00005 | d00006 | d00007 | ... |
|---|---|---|---|---|---|---|---|---|
| 2015/2/19 17:05 00 | 2.10 | 6.51 | Na | Na | Na | Na | Na | |
| 2015/2/19 17:05 01 | 2.12 | 4.37 | 3.68 | Na | Na | Na | Na | |
| 2015/2/19 17:05 02 | 1.63 | 3.67 | 3.32 | 1.52 | Na | Na | Na | |
| 2015/2/19 17:05 03 | 0.41 | 4.27 | 5.59 | 0.01 | Na | Na | Na | |
| 2015/2/19 17:05 04 | Na | 6.43 | 7.62 | 0.02 | 0.85 | Na | Na | |
| 2015/2/19 17:05 05 | Na | 4.51 | 8.77 | 0.44 | 1.98 | Na | Na | |
| 2015/2/19 17:05 06 | Na | Na | 7.36 | 7.67 | 1.37 | 4.67 | 4.19 | |
| 2015/2/19 17:05 07 | Na | Na | 6.68 | 7.19 | 4.85 | 2.73 | 6.67 | |
| 2015/2/19 17:05 08 | Na | Na | 4.32 | Na | Na | 1.74 | 5.23 | |
| ⋮ | ⋮ | | | | | | | |

231

SPEED INFORMATION

*FIG. 6*

| MEASUREMENT DATE AND TIME | Player001 | Player002 | Player003 | Player004 | ... |
|---|---|---|---|---|---|
| 2015/2/19 17:05 00 | 1.12 | 7.51 | 5.32 | 2.01 | |
| 2015/2/19 17:05 01 | 1.32 | 5.37 | 3.68 | 1.66 | |
| 2015/2/19 17:05 02 | 2.67 | 1.83 | 2.22 | 1.18 | |
| 2015/2/19 17:05 03 | 4.67 | 0.11 | 6.89 | 0.06 | |
| 2015/2/19 17:05 04 | 6.63 | 0.55 | 8.92 | 0.06 | |
| 2015/2/19 17:05 05 | 5.21 | 1.18 | 8.67 | 0.55 | |
| 2015/2/19 17:05 06 | 4.77 | 1.17 | 6.19 | 2.66 | |
| 2015/2/19 17:05 07 | 2.33 | 4.15 | 7.97 | 4.11 | |
| 2015/2/19 17:05 08 | 1.24 | 2.68 | 6.25 | 3.55 | |
| : | : | | | | |

BEHAVIOR INFORMATION

FIG. 7

USER ID

Player001

| MEASURE-MENT DATE AND TIME | x COORDI-NATE | y COORDI-NATE |
|---|---|---|
| 2015/2/19 17:05 00 | 7.10 | 6.51 |
| 2015/2/19 17:05 01 | 3.12 | 4.37 |
| 2015/2/19 17:05 02 | 1.63 | 4.52 |
| 2015/2/19 17:05 03 | 4.41 | 5.73 |
| 2015/2/19 17:05 04 | 4.11 | 4.51 |
| 2015/2/19 17:05 05 | 4.43 | 6.37 |
| 2015/2/19 17:05 06 | 5.16 | 7.54 |
| 2015/2/19 17:05 07 | 4.41 | 5.54 |
| 2015/2/19 17:05 08 | 3.10 | 5.16 |
| ⋮ | ⋮ | ⋮ |

Player002

| x COORDI-NATE | y COORDI-NATE |
|---|---|
| 15.76 | 6.51 |
| 14.73 | 8.65 |
| 15.42 | 10.22 |
| 14.45 | 12.23 |
| 14.62 | 12.55 |
| 14.41 | 12.27 |
| 15.16 | 12.15 |
| 14.71 | 13.44 |
| 12.80 | 14.11 |
| ⋮ | ⋮ |

Player003

| x COORDI-NATE | y COORDI-NATE |
|---|---|
| 36.74 | 26.44 |
| 34.23 | 26.15 |
| 32.65 | 23.26 |
| 31.45 | 22.12 |
| 28.21 | 21.28 |
| 24.56 | 20.27 |
| 23.55 | 23.13 |
| 23.15 | 23.90 |
| 23.87 | 23.83 |
| ⋮ | ⋮ |

...

INDIVIDUAL TRACK INFORMATION

*FIG. 11*

352 — ENVIRONMENT INFORMATION INPUT PAGE (316, 317, 318)

| ACTIVITY ID | ACTIVITY NAME | START TIME POINT | FINISH TIME POINT | AREA NAME | PARTICIPANT | GROUPING |
|---|---|---|---|---|---|---|
| 1 | DRIBBLING PRACTICE | 15:00 00 | 15:15 00 | ○○GROUND ▼ | ☑ ALL / ☐ INDIVIDUAL SELECTION | ☑ NONE / ☐ ADVANCED SETTINGS |
| 2 | PASSING PRACTICE | 15:20 00 | 15:35 00 | ○○GROUND ▼ | ☑ ALL / ☐ INDIVIDUAL SELECTION | ☑ NONE / ☐ ADVANCED SETTINGS |
| 3 | PASSING GAME 1 | 15:40 00 | 16:00 00 | ××GROUND ▼ | ☐ ALL / ☑ INDIVIDUAL SELECTION | ☐ NONE / ☑ ADVANCED SETTINGS |
| 4 | PASSING GAME 2 | 16:05 00 | 16:25 00 | ××GROUND ▼ | ☐ ALL / ☑ INDIVIDUAL SELECTION | ☐ NONE / ☑ ADVANCED SETTINGS |
| ⋮ | ⋮ | ⋮ | ⋮ | ⋮ | ⋮ | ⋮ |

319 — PARTICIPANT SELECTION PAGE

| SELECTION | USER ID | USER NAME | UNIFORM NUMBER | POSITION IN TEAM | SCHOOL GRADE | ... |
|---|---|---|---|---|---|---|
| ☐ | Player001 | ○○○○ | 1 | GK | 2 | ... |
| ☑ | Player002 | ×××× | 2 | DF | 1 | ... |
| ☑ | Player003 | △△△△ | 3 | DF | 3 | ... |
| ☑ | Player004 | ●●●● | 4 | MF | 3 | ... |
| ⋮ | ⋮ | ⋮ | ⋮ | ⋮ | ⋮ | ⋮ |

320 — GROUPING SELECTION PAGE

| USER ID | USER NAME | TEAM A | TEAM B | TEAM C | ·· |
|---|---|---|---|---|---|
| Player001 | ○○○○ | ☑ | ☐ | ☐ | ·· |
| Player002 | ×××× | ☐ | ☑ | ☐ | ·· |
| Player003 | △△△△ | ☑ | ☐ | ☐ | ·· |
| Player004 | ●●●● | ☐ | ☑ | ☐ | ·· |
| ⋮ | ⋮ | ⋮ | ⋮ | ⋮ | ⋮ |

*FIG. 17*

ENVIRONMENT INFORMATION — 27

| TABLE NAME | ACTIVITY INFORMATION TABLE |
|---|---|

206

| No. | LOGIC NAME |
|---|---|
| 1 | ACTIVITY ID | — 2061
| 2 | ACTIVITY NAME | — 2062

| TABLE NAME | ENVIRONMENT INFORMATION TABLE |
|---|---|

207

| No. | LOGIC NAME |
|---|---|
| 1 | ACTIVITY ID | — 2071
| 2 | START TIME POINT | — 2072
| 3 | FINISH TIME POINT | — 2073
| 4 | AREA ID | — 2074
| 5 | USER ID (MULTIPLE) | — 2075

*FIG. 18*

| 328 | 329 | 330 |
|---|---|---|
| TEAM A ▼ | PASSING PRACTICE ▼ | TIME : 15:00:00 ~ 15:15:00 LOCATION : ○○GROUND A |

| UNIFORM NUMBER | NAME | DISTANCE TRAVELED [km] | DRIBBLING DISTANCE [km] | TOP SPEED [km/h] | DRIBBLING SPEED [km/h] | MAXIMUM EXERCISE INTENSITY [METs] | NUMBER OF SPRINTS | NUMBER OF KICKS | NUMBER OF JUMPS |
|---|---|---|---|---|---|---|---|---|---|
| 1 | Player 001 | 0.55 | 0.08 | 22.18 | 8.02 | 8.32 | 6 | 10 | 0 |
| 2 | Player 002 | 1.55 | 0.12 | 21.18 | 8.02 | 8.32 | 6 | 16 | 0 |
| 3 | Player 003 | 2.12 | 0.22 | 24.22 | 5.57 | 7.33 | 7 | 10 | 1 |
| 4 | Player 004 | 0.93 | 0.15 | 26.15 | 6.81 | 9.66 | 7 | 22 | 2 |
| ⋮ | ⋮ | ⋮ | ⋮ | ⋮ | ⋮ | ⋮ | ⋮ | ⋮ | ⋮ |

STATE OF ATHLETIC ACTIVITY [%]

▨ STANDING STILL ▥ WALKING ⋯ JOGGING ≡ SPRINTING □ DRIBBLING

| Player | Standing Still | Walking | Jogging | Sprinting | Dribbling |
|---|---|---|---|---|---|
| Player001 | 40.1 | 35.2 | 10.4 | 10.6 | 3.7 |
| Player002 | 50.5 | 20.1 | 20.8 | 5.7 | 2.9 |
| Player003 | 35.3 | 22.8 | 18.5 | 19.2 | 4.2 |
| Player004 | 40.1 | 22.9 | 22.5 | 8.3 | 6.2 |

FIG. 21

| MENU | TIME | DISTANCE TRAVELED [km] | DRIBBLING DISTANCE [km] | TOP SPEED [km/h] | DRIBBLING SPEED [km/h] | MAXIMUM EXERCISE INTENSITY [METs] | NUMBER OF SPRINTS | NUMBER OF KICKS | NUMBER OF JUMPS |
|---|---|---|---|---|---|---|---|---|---|
| DRIBBLING PRACTICE | 15:00 00 ~ 15:15 00 | 1.21 | 0.99 | 24.82 | 20.21 | 12.67 | 7 | 2 | 0 |
| PASSING PRACTICE | 15:20 00 ~ 15:35 00 | 0.55 | 0.08 | 22.18 | 8.02 | 8.32 | 6 | 10 | 0 |
| PASSING GAME 1 | 15:40 00 ~ 16:00 00 | 0.81 | 0.22 | 29.82 | 5.55 | 10.21 | 8 | 17 | 1 |
| PASSING GAME 2 | 16:05 00 ~ 16:25 00 | 0.75 | 0.15 | 22.55 | 6.81 | 8.11 | 5 | 12 | 2 |
| ⋮ | ⋮ | ⋮ | ⋮ | ⋮ | ⋮ | ⋮ | ⋮ | ⋮ | ⋮ |
STATE OF ATHLETIC ACTIVITY [%]
STANDING STILL | WALKING | JOGGING | SPRINTING | DRIBBLING
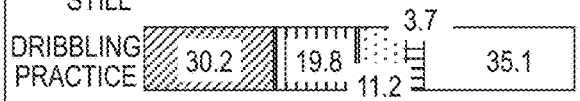
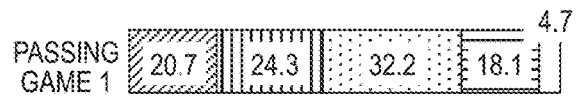
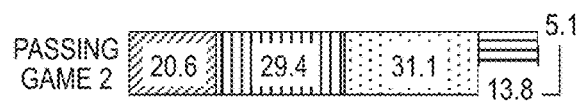
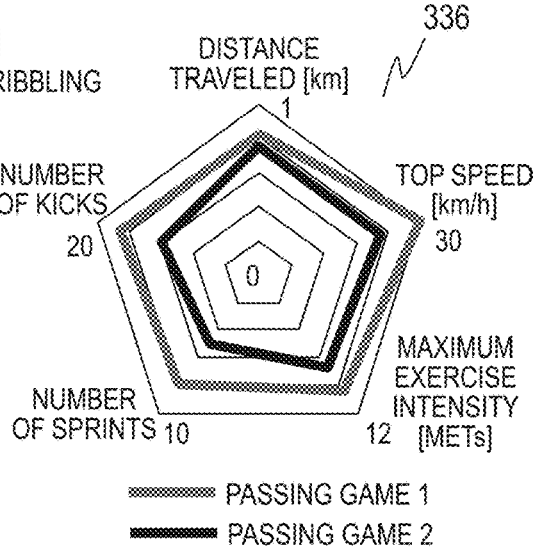
FIG. 22

ANALYSIS SYSTEM AND ANALYSIS METHOD

CLAIM OF PRIORITY

The present application claims priority from Japanese patent application JP2015-118347 filed on Jun. 11, 2015, the content of which is hereby incorporated by reference into this application.

BACKGROUND

The subject matter discussed herein relates to an analysis system and an analysis method. With the technological advances in various sensors and measurement apparatus, attention is being paid to sensing of behavior information and track information even in fields in which sensing has hitherto not been utilized, such as sports and education. However, current technology is mainly for measuring human flows and traffic flows by using cameras or lasers. With the current technology, it is not possible to monitor performance in sports or to sufficiently acquire detailed information on the tracks and movements of each individual in a group, which is required for communication analysis and the like in education.

As the related art, there is a technology in which moving object position data of a player (one person) is collected by using two laser radars, and sequentially stored to generate moving object track data. Further, there is a technology in which moving object track video data is generated and output by superimposing a player in video data and moving object track data.

In addition, as the related art, there is a technology in which a sensor module (accelerometer, magnetometer, or Global Positioning System (GPS)) is mounted on a subject (user, or piece of exercise equipment to be used by the user), and performance during an exercise (team game) is evaluated and presented. Based on this technology, a position and a track of the subject during the exercise can be measured by using GPS. Through use of such information together with other sensing data, track information and performance information beneficial for evaluating the exercise being performed by the subject wearing the sensor module can be output.

Further, a method has been proposed in which an entire game area is divided up and photographed by a plurality of image pickup cameras, a specific wavelength radiation member is mounted, or, just a coated target is extracted, and a tracking position is visualized (e.g., refer to JP 10-276351 A). Based on the technology disclosed in JP 10-276351 A, the movements or a movement track of only a specified player, ball, and the like can be displayed by, for example, superimposing tracking position information over a schematically-illustrated image of the ground (playing field).

SUMMARY

With a technology in which track information on a player (one person) is measured by using a plurality of laser radars, there is a problem in that not every piece of track information can be detected during a group game.

Further, when a technology is used in which the position and the track of a moving subject are measured using GPS, because GPS has a low position detection accuracy, in sports requiring highly accurate position information, the position cannot be detected to the required level. In addition, there are also difficulties in detecting track information for games that are played indoors, in which it is difficult to receive satellite radio waves.

Still further, when the technology disclosed in JP 10-276351 A is used, when the lighting is dark, such as during bad weather or during a night game, fewer signals are reflected by the specific wavelength radiation member. As a result, depending on the used environment, the accuracy with which the individuals are distinguished from each other by a marker using the specific wavelength radiation member deteriorates, which can prevent the position from being detected sufficiently accurately.

Thus, in the related art, there is a problem in that, regardless of the environment or the field, it is not possible to correctly measure every complex movement and track of a group.

For solving the above problem, an embodiment of this invention includes a storage module configured to store a track indicating in time series a position of an individual that is moving as track data, and store sensor data indicating in time series a measurement result of the individual by a sensor worn by the individual; a speed calculation module configured to calculate a speed index indicating a movement speed of the individual based on the track data; an index calculation module configured to calculate a behavior index indicating a movement intensity of the individual based on the sensor data; a similarity degree calculation module configured to calculate a degree of similarity between the speed index and the behavior index based on changes in time series of the speed index and the behavior index; and an association module configured to associate the track and the individual on which the sensor data has been measured based on the degree of similarity.

According to this invention, each complex movement and track in a group can be correctly measured for any environment and any field. The problems to be solved by this invention, the structures, and the advantageous effects other than those described above according to this invention are made clear based on the following description of the embodiments.

The details of one or more implementations of the subject matter described in the specification are set forth in the accompanying drawings and the description below. Other features, aspects, and advantages of the subject matter will become apparent from the description, the drawings, and the claims.

BRIEF DESCRIPTION OF THE DRAWINGS

FIG. 3 is an explanatory diagram for showing the track information according to the first embodiment.

FIG. 6 is an explanatory diagram for showing the speed information according to the first embodiment.

FIG. 7 is an explanatory diagram for showing the behavior information according to the first embodiment.

FIG. 11 is an explanatory diagram for showing the individual track information generated by the track generation module according to the first embodiment.

FIG. 17 is an explanatory diagram for showing a screen displayed by the environment information input module according to the second embodiment.

FIG. 18 is an explanatory diagram for showing the environment information according to the second embodiment.

FIG. 21 is an explanatory diagram for showing a screen generated based on the speed information according to the first embodiment.

FIG. 22 is an explanatory diagram for showing a screen for displaying an analysis result of the performance of one user according to the second embodiment.

DETAILED DESCRIPTION OF THE PREFERRED EMBODIMENTS

Now, embodiments of this invention are described with reference to the drawings.

First Embodiment

As a preferred first embodiment of this invention, track monitoring during a game in an athletic activity is described with reference to the drawings.

Figure 1:
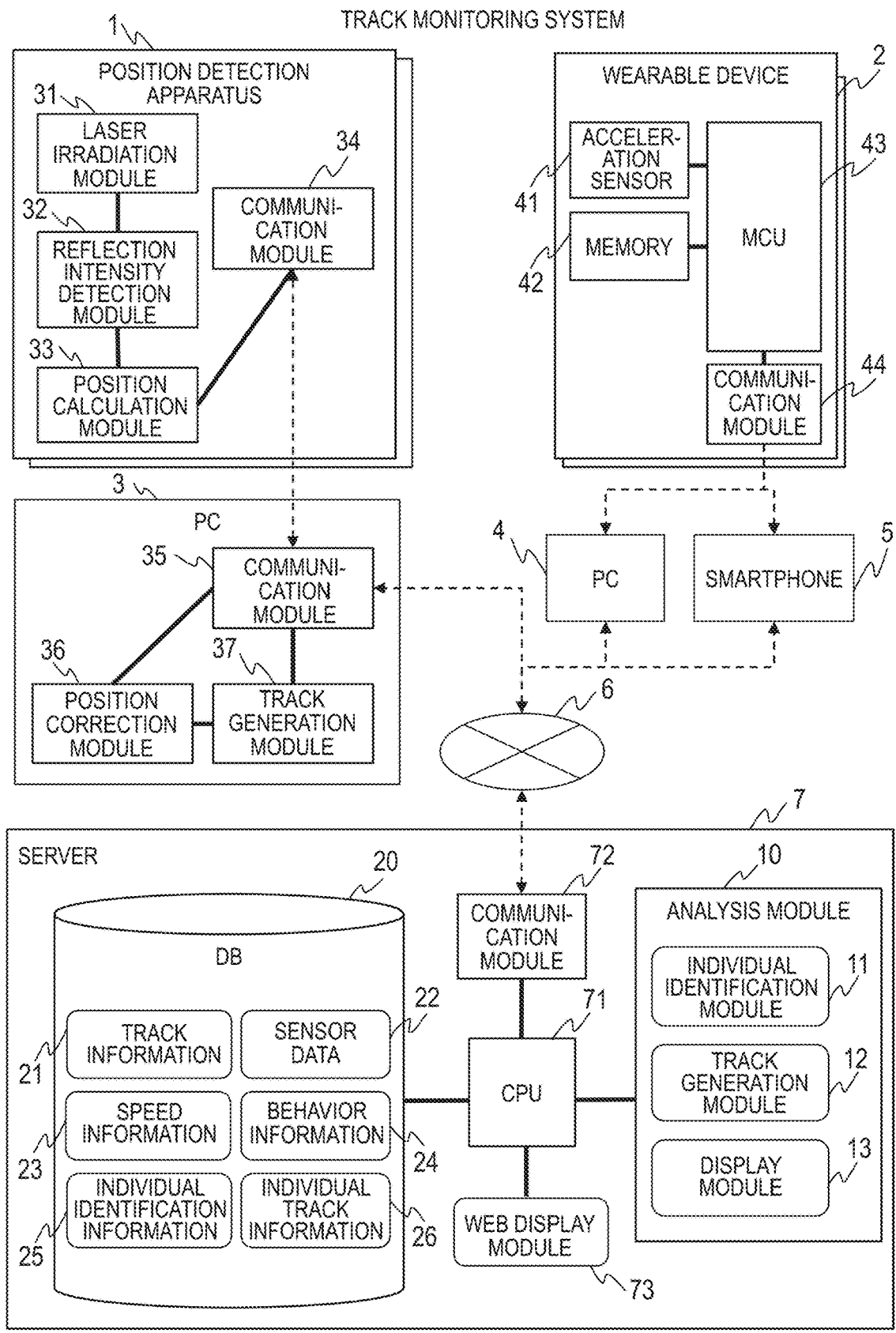
FIG. 1 is a block diagram for illustrating a configuration of a track monitoring system according to the first embodiment.

FIG. 1 is a block diagram for illustrating a configuration of a track monitoring system according to the first embodiment.

The track monitoring system according to the first embodiment is configured to acquire a track of the movements of an individual, in particular, the movements of an individual included in a group. It should be noted that, in the following, a system configured to acquire a track of the movements of a person is described. However, this invention may be applied to any system configured to acquire a track of an individual that moves in an irregular manner, such as an animal. Further, in the following, the individual for which a track is acquired, in particular, is referred to as a "user".

The track monitoring system includes a position detection apparatus 1, a personal computer (PC) 3, a wearable device 2, a PC 4, a smartphone 5, and a server 7.

The server 7 is configured to perform communication to and from the PC 3, the PC 4, and the smartphone 5 via a network 6. The server 7 is a computer including a central processing unit (CPU) 71, a communication module 72, a Web display module 73, an analysis module 10, and a database (DB) 20.

The server 7 is configured to realize functions of the analysis module 10, the communication module 72, and the Web display module 73 by the CPU 71 executing a program stored in a memory. Memories of the server 7 include a read-only memory (ROM), which is a non-volatile storage device, and a random-access memory (RAM), which is a volatile storage device.

The ROM stores therein an invariable program (for example, a basic input/output system (BIOS)) or the like. The RAM is a high-speed volatile storage element such as a dynamic random access memory (DRAM) and is configured to temporarily store therein a program stored in an auxiliary storage device, and data to be used in executing the program.

The database 20 is stored in the auxiliary storage device. The auxiliary storage device is, for example, a large-scaled nonvolatile storage device such as a magnetic storage device (HDD) or a flash memory (SDD). Further, the auxiliary storage device is configured to store therein a program to be executed by the CPU 71 and data to be used in executing the program. In other words, the program is read out from the auxiliary storage device to be loaded into the memory, and is executed by the CPU 71.

The analysis module 10 is a function module configured to associate a track detected by the position detection apparatus 1 and an individual wearing the wearable device 2 based on track information 21 and sensor data 22. The analysis module 10 mainly includes function modules of an individual identification module 11, a track generation module 12, and a display module 13.

The Web display module 73 is configured to output data recorded in the database 20 to the PC 4 and the smartphone 5 via the network 6 so that the data is available to an operator who wishes to acquire a track of the movements of an individual.

The communication module 72 is an interface configured to control communication to and from another apparatus in accordance with a predetermined protocol. The communication module 72 is capable of transmitting and receiving data by communicating to and from another apparatus via the network 6.

The analysis module 10, the Web display module 73, and the communication module 72 may each be realized by a program, or may each be realized by a physical integrated circuit. In particular, the analysis module 10 may be realized by a plurality of programs or by a plurality of integrated circuits for executing the function modules included in the analysis module 10. Further, the individual identification module 11, the track generation module 12, and the display module 13 may be realized by a plurality of programs or a plurality of integrated circuits for each process to be executed by each of those modules.

A program to be executed by the CPU 71 is provided to the server 7 through a removable medium (such as a CD-ROM or a flash memory) or a network, and is then stored in the auxiliary storage device as a non-transitory storage medium. For this reason, it is preferred that the server 7 have an interface through which data is read from the removable medium.

The server 7 is a computer system which is physically configured on one computer or which is configured on a plurality of logical or physical computers. In addition, the above-mentioned programs may be operated in separate threads on the same computer, or may be operated on a virtual computer constructed on a plurality of physical computer resources.

The database 20 is configured to store, as data, the track information 21, the sensor data 22, speed information 23, behavior information 24, individual identification information 25, and individual track information 26. The track information (track data) 21 is collected from the position detection apparatus 1. The track information 21 indicates a track generated during an athletic activity by a group. The track according to this embodiment indicates a position of a moving individual in time series.

The sensor data 22 is collected from the wearable device 2. The sensor data 22 indicates a measurement result relating to an individual measured by the wearable device 2 that the individual is wearing.

The individual track information 26, which is generated by the analysis module 10 based on the track information 21 and the sensor data 22, indicates a track for each individual.

The position detection apparatus 1 is an apparatus configured to detect objects mainly by using laser light. The track monitoring system according to the first embodiment may include a plurality of position detection apparatus 1. Each position detection apparatus 1 includes, as function modules, a laser irradiation module 31, a reflection intensity detection module 32, a position calculation module 33, and a communication module 34.

The position detection apparatus 1 may also have a computer including a processor and a memory. Each of the function modules of the position detection apparatus 1 may be realized by the processor executing a program. Further, the position detection apparatus 1 may include a physical apparatus for realizing each function module.

The laser irradiation module 31 is configured to radiate laser light. The reflection intensity detection module 32 is configured to measure, when an object is present in an irradiation range of the irradiated laser light, the intensity of the laser light reflected by the object. Further, the position calculation module 33 is configured to identify the position of the object based on the intensity of the reflected laser light, and to generate track information on a track indicating the position of the object in time series by identifying the position of the object at a plurality of measurement time points. The communication module 34 is configured to transmit the track information generated by the position calculation module 33 to the PC 3 wirelessly or by using a cable.

The PC 3 is a computer configured to determine the track of an individual included in a group. The PC 3 mainly includes, as function modules, a communication module 35, a position correction module 36, and a track generation module 37. The PC 3 is a computer including a processor and a memory. Each of the function modules of the PC 3 may be realized by the processor executing a program. Further, the PC 3 may include a physical apparatus for realizing each function module.

The position correction module 36 is configured to correct track information received from a plurality of position detection apparatus 1. The track generation module 37 is configured to generate track information by sequentially accumulating temporal track information. The communication module 35 is configured to transmit the track information generated by the track generation module 37 to the server 7 via the network 6.

The network 6 may be any type of network. For example, the network 6 may be the Internet, or a peer-to-peer (P-2-P) network.

The wearable device 2 is a device worn by an individual whose position is to be detected. The wearable device 2 mainly includes an acceleration sensor 41, a memory 42, a microcontroller (MCU) 43, and a communication module 44.

The acceleration sensor 41 is configured to measure the acceleration of a user about 20 to 1,000 times per second, for example. The microcontroller 43 is configured to record the measurement result measured by the acceleration sensor 41 in the memory 42 as sensor data. In this case, the microcontroller 43 is configured to record, as the sensor data, an identifier (user ID) unique to the user and the measurement result.

It should be noted that the wearable device 2 may be configured to measure any type of content as the sensor data, as long as the value of such content changes as a result of movements by the user. The content to be measured by the wearable device 2 is described later.

In addition, the microcontroller 43 is configured to transmit the sensor data recorded in the memory 42 to the PC 4 and the smartphone 5 via the communication module 44. The communication module 44 is configured to transmit, wirelessly or by using a cable, the sensor data to the PC 4 or the smartphone 5 at a timing at which communication can be performed, or at an arbitrary timing determined by the user.

The PC 4 and the smartphone 5 are configured to communicate to and from the wearable device 2, and when sensor data has been received, to transfer the sensor data to the server 7. The PC 4 is a computer including a processor, a memory, and a network interface. The smartphone 5 is a tablet terminal.

It should be noted that the server 7, the PC 3, and the PC 4 illustrated in FIG. 1 are coupled via the network 6. However, the server 7 according to this embodiment may also include the function of at least one of the PC 3 and the PC 4. This enables the track monitoring system to analyze the data measured by the position detection apparatus 1 and the wearable device 2 without transmitting the data to the server 7 via the network 6, thereby improving response speed. Further, because in such a case there is no need to arrange a server 7 to be coupled to the network 6, the track of an individual can be monitored easily.

Figure 2:
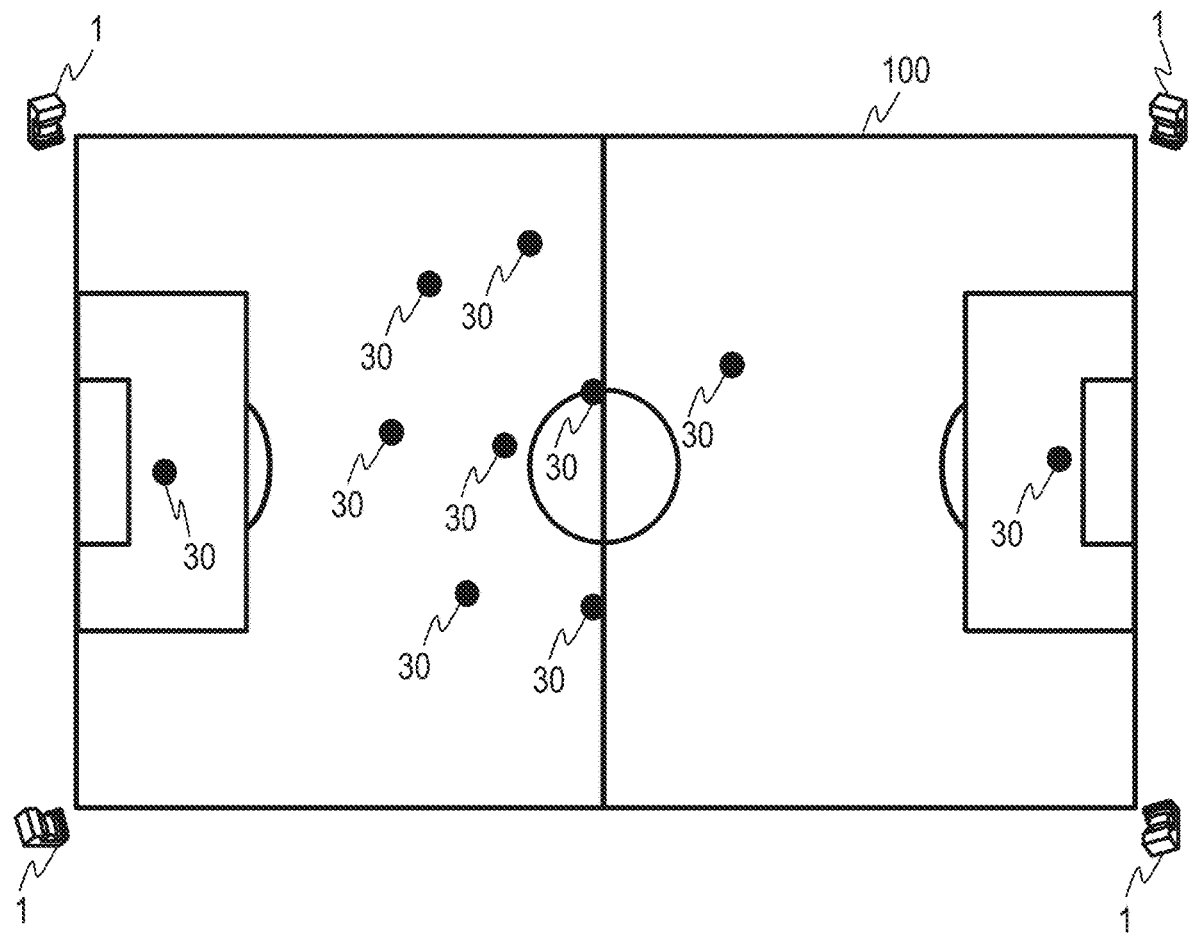
FIG. 2 is an explanatory diagram for illustrating an example in which the position detection apparatus according to the first embodiment is arranged.

FIG. 2 is an explanatory diagram for illustrating an example in which the position detection apparatus 1 according to the first embodiment is arranged.

In the first embodiment, the athletic activity in which a track is acquired is soccer. However, the type of athletic activity in which a track is to be acquired may be any game played on a field or a court. The track monitoring system according to the first embodiment may be applied to group games such as rugby, basketball, volleyball, goalball, baseball, tennis, handball, lacrosse, track and field, and speed skating. Further, the track monitoring system according to the first embodiment may also be applied to individual games such as figure skating, gymnastics, and skiing.

The position detection apparatus 1 according to the first embodiment is a laser radar capable of detecting the position of an object based on reflection of laser light. One or more position detection apparatus 1 are arranged at positions capable of measuring the whole of a game area 100.

It is desired that the position detection apparatus 1 be arranged at a position at which the laser light irradiated from the laser irradiation module 31 and the plane of the field are horizontal. However, when the position calculation module 33 of the position detection apparatus 1 and the position correction module 36 of the PC 3 correct position coordinates, the position detection apparatus 1 may be arranged in various locations, such as the spectator seating of a stadium or a gymnasium, a sloped ski run, and the like.

Further, the position detection apparatus 1 may also be an apparatus configured to measure the position of an object based on video analysis, rather than on laser light. The position detection apparatus 1 may be any apparatus, as long as the apparatus is capable of measuring a position. In addition, the position detection apparatus 1 may be configured to detect a stride length, the number of strides, and the like, along with position. These pieces of detected information may be transmitted to the server 7 as track information.

One or more of the wearable device 2 is/are worn on the body of a user 30 performing an athletic activity. As the wearable device 2, the user in the first embodiment wears directly on his or her wrist a wristwatch-type wearable device including a triaxial acceleration sensor. The user 30 is the individual whose track is to be detected in this embodiment, and, the individual to be measured by the wearable device 2.

The wearable device 2 includes at least one or more sensors selected from among various sensors. Examples of the various sensors include, but are not limited to, an acceleration sensor, a gyro sensor, a pedometer, a heart rate monitor, a position sensor, a shock sensor, a magnetometer, a temperature sensor, a humidity sensor, a wind sensor, a sound sensor, an air pressure sensor, and an infrared sensor. Further, the results measured by those various sensors may be transmitted to the server 7 as sensor data.

In addition, the user 30 may wear the wearable device 2 on a portion of his or her body, such as the head, neck, shoulder, back, arm, wrist, hand, finger, waist, hip, leg, ankle, foot, heel, toe, and the like, so that the wearable device 2 is physically connected thereto. Further, when there is one or more layers of clothing, footwear, or sports protective equipment present between the wearable device 2 and the body of the user 30, the user 30 may wear the wearable device 2 by using various removable or non-removable connecting means, such as a strap, an adhesive, a pocket, a clip, and the like, under a state in which the wearable device 2 and the clothing, footwear, or sports protective equipment to be used in the athletic activity are integrated.

The track information measured by the position detection apparatus 1 is transmitted to the server 7 via the PC 3, and stored by the server 7 in the track information 21 in the database 20. Similarly, the sensor data measured by the wearable device 2 is transmitted to the server 7 via the PC 4 or the smartphone 5, and stored by the server 7 in the sensor data 22 in the database 20.

FIG. 3 is an explanatory diagram for showing the track information 21 according to the first embodiment.

The track information 21 includes an area table 201, a track line table 202, and a track information table 203. The area table 201 is for recording information on the location for detecting track information. The track line table 202 is for recording information from an appearance position until a disappearance position of the track for each track ID. The track information table 203 is for recording position information for each time point of one track.

The area table 201 includes an area identification (ID) 2011, an area name 2012, and area apex coordinates 2013. The area ID 2011 indicates an ID assigned to each measured location in order to recognize the location at which the track information was measured. The area name 2012 indicates the name of the location at which track information was measured. The Web display module 73 can use the area name 2012 to display the area name on the PC 4, for example.

The area apex coordinates 2013 are for storing the position coordinates of a measurement area defined using a spatial reference system World Geodetic System (WGS) 84. Examples of the spatial reference system that may be used to define the position coordinates of the area may include, but are not limited to, Japanese Geodetic Datum (JGD) 2000, JGD 2011, or Tokyo.

The track line table 202 includes a track ID 2021, a start time point 2022, a finish time point 2023, and a track coordinates row 2024. The track ID 2021 indicates an ID assigned to each measured track in order to recognize the tracks generated by the position detection apparatus 1.

The start time point 2022 is for recording the time point at which the track appeared. The finish time point 2023 is for recording the time point at which the track disappeared. The track coordinates row 2024 is for storing the coordinates at each time point from the appearance position until the disappearance position of the track in a LINESTRING.

The track information table 203 includes a track ID 2031, a measurement date and time 2032, an x coordinate 2033, a y coordinate 2034, and an area ID 2035. The track ID 2031 corresponds to the track ID 2021 in the track line table 202.

The measurement date and time 2032 indicates the time points of the period during which the track is measured. The x coordinate 2033 and the y coordinate 2034 indicate position information on the position at which the track indicated by the track ID 2031 is present at the date and time indicated by the measurement date and time 2032. The area ID 2035 corresponds to the area ID 2011 in the area table 201.

Figure 4:
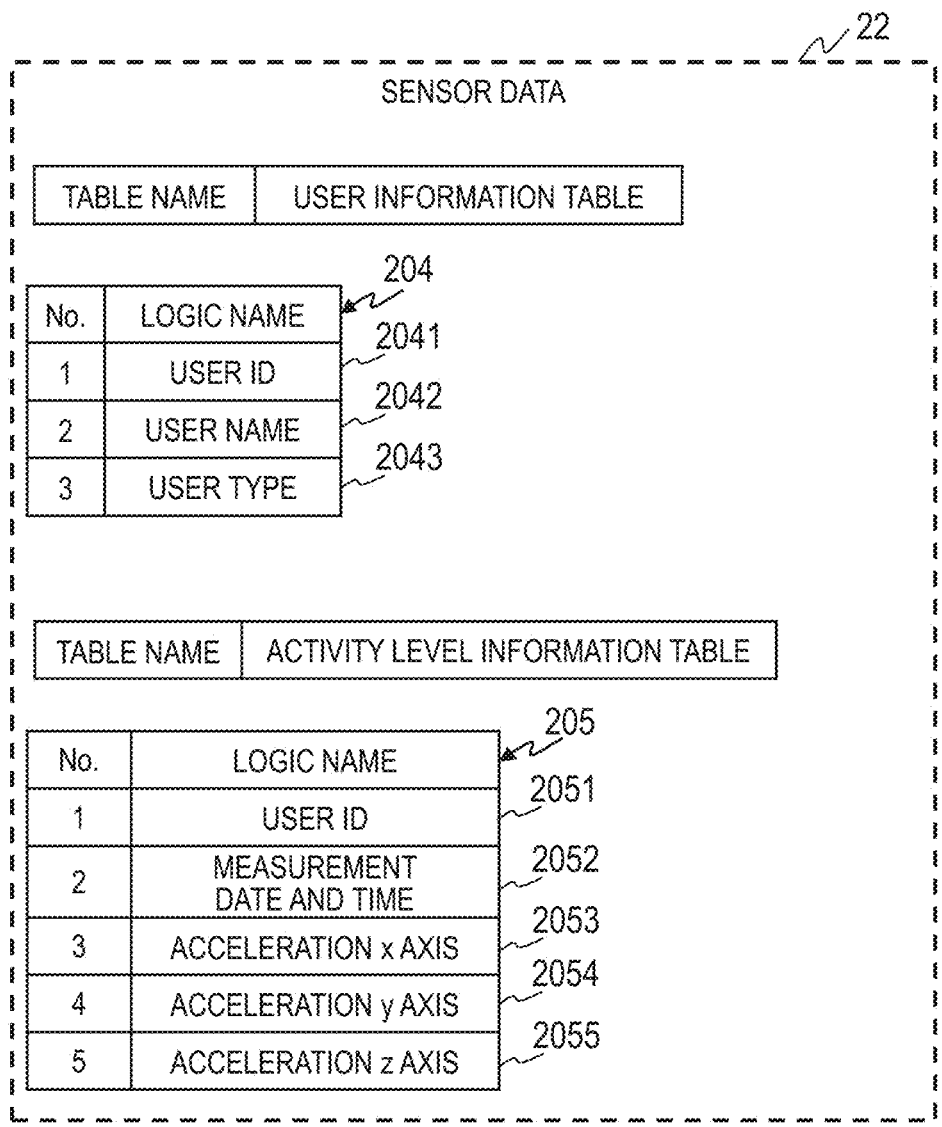
FIG. 4 is an explanatory diagram for showing the sensor data according to the first embodiment.

FIG. 4 is an explanatory diagram for showing the sensor data 22 according to the first embodiment.

The sensor data 22 includes a user information table 204 for recording information on the user 30 wearing the wearable device 2, and an activity level information table 205 for recording activity level information on each user 30.

The user information table 204 includes a user ID 2041, a user name 2042, and a user type 2043. The user ID 2041 is for recording an ID assigned to each user 30 in order to recognize the user 30 wearing the wearable device 2. The user ID stored by the user ID 2041 is stored in the sensor data transmitted from the wearable device 2.

The user name 2042 is for recording a name or a nickname of the user 30 wearing the wearable device 2. The user type 2043 is for recording age, gender, and the like, or various types of other information on the user 30, as user information.

For example, when the athletic activity to be measured is soccer, recording the team that the user belongs to, the user's role (position) in the team, and the like in the user type 2043 enables the Web display module 73 to display an evaluation and an indication of each type.

One line of the activity level information table 205 shows the information on one user 30 at one time point. The activity level information table 205 includes a user ID 2051, a measurement date and time 2052, an acceleration x axis 2053, an acceleration y axis 2054, and an acceleration z axis 2055. The user ID 2051, which is for recording an ID in order to recognize the user 30, corresponds to the user ID 2041.

The measurement date and time 2052 stores the date and time at which the sensor data was measured. The acceleration x axis 2053, the acceleration y axis 2054, and the acceleration z axis 2055 are for storing the measurement results of the triaxial acceleration sensor.

Figure 5:
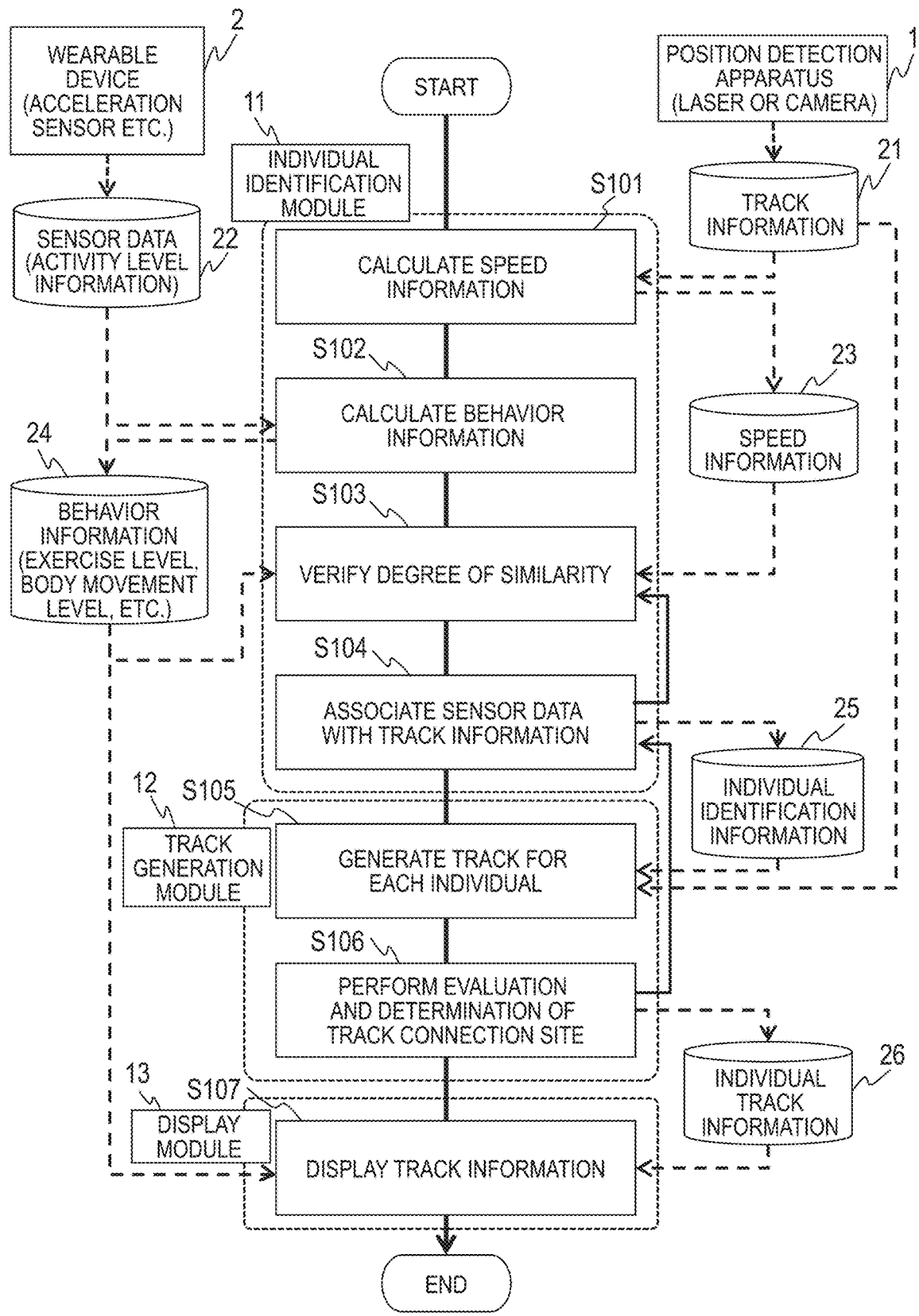
FIG. 5 is a flowchart for illustrating an outline of processing performed by the analysis module according to the first embodiment.

FIG. 5 is a flowchart for illustrating an outline of processing performed by the analysis module 10 according to the first embodiment.

First, the individual identification module 11 calculates the speed information 23 indicating the speed of movement of the user 30 of each track based on the group track information 21 recorded in the database 20 (S101). It should be noted that any method may be employed as the method of calculating the speed information 23. Speed information 23 indicating a movement distance per unit time can also be calculated. Further, when the stride length and the number of strides are to be included in the track information, the speed information 23 may be calculated based on the stride length and the number of strides.

In addition, the individual identification module 11 calculates the behavior information 24, which has a large correlation with the speed during the athletic activity, based on the sensor data 22 recorded in the database 20 (S102).

The behavior information 24 indicates, for example, a characteristic level, such as an exercise level, a body movement level, and the like, having a value that changes in accordance with the intensity of movement (or magnitude of movement energy) by the user 30. Further, the behavior information 24 indicates change in the characteristic level in time series.

Next, the individual identification module 11 verifies a degree of similarity by using the calculated speed information 23 and the calculated behavior information 24 (S103). Further, based on the result of Step S103, the individual identification module 11 generates individual identification information 25 by associating the group track information 21 and the sensor data 22 (S104).

The track generation module 12 generates individual track information 26, which is sequential in time, by connecting the group track information 21, which is non-sequential in time and indicates a track, by using the individual identification information 25 generated by the individual identification module 11 and the group track information 21 (S105). In addition, the track generation module 12 calculates a distance between the start point and the finish point of the track information at each connected site of the individual track information 26 generated in Step S105. Then, based on the calculated distance, the track generation module 12 evaluates the correctness of the track (S106).

In this case, as a result of the evaluation, when it is determined that the connection site is not correct, the track generation module 12 finishes the processing, and instructs the individual identification module 11 to again associate the group track information 21 of the individual identification information 25 and the sensor data 22. The individual identification module 11 again executes Step S105 in accordance with the instruction.

When it is determined by the track generation module 12 as a result of the evaluation that the connection site is correct, the display module 13 generates a screen for displaying the track and the performance of the individual by associating the individual track information 26 generated by the track generation module 12 with various types of information, such as body orientation, movement, and fatigue estimated from the sensor data 22.

The information that can be associated with the individual track information 26 is not limited to the above-mentioned information on body orientation, movement, and fatigue. Any information may be associated with the individual track information 26, as long as such information is estimated from the sensor data 22 measured simultaneously with the track information.

Executing the processing illustrated in FIG. 5 enables the analysis module 10 to accurately associate the behavior information 24 and the track of the user 30 by using the track information 21 detected by the position detection apparatus 1 and the sensor data 22 measured by the wearable device 2. As a result, each complex movement and the track of the user 30 can be accurately measured even during a group athletic activity in which a plurality of tracks are detected.

The processing illustrated in FIG. 5 is now described in more detail.

In Step S101, the individual identification module 11 calculates distance based on the track information table 203 in the group track information 21 recorded in the database 20, and calculates the speed information 23 by time differentiation of the calculated distance. Specifically, the individual identification module 11 identifies an entry in the track information table 203 having the same track ID 2031, and determines a times series of the position information based on the measurement date and time 2032, the x coordinate 2033, and the y coordinate 2034 of the identified entry. Further, the individual identification module 11 determines speed based on the determined times series of the position information.

FIG. 6 is an explanatory diagram for showing the speed information 23 according to the first embodiment.

The speed information 23 includes a measurement date and time 231 and speed information 232. The measurement date and time 231 indicates the date and the time point at which the track information 21 was measured. The speed information 232 indicates speed information calculated based on the track information 21 measured at the measurement date and time 231. A value for the speed information 232 is stored for each track ID.

In the speed information 23 shown in FIG. 6, one row indicates the speed of a plurality of tracks at one measurement time, and one column indicates the speed of one track in times series. The track information 21 and the speed information 23 has a feature that the user 30 is not identified and the information is temporally fragmented.

It should be noted that the individual identification module 11 is configured to calculate the speed information 23 for each predetermined time interval. The speed information 23 shown in FIG. 6 is a result calculated by the individual identification module 11 every second. The individual identification module 11 may also be configured to calculate the speed information 23 for any time interval.

In Step S102, the individual identification module 11 calculates the behavior information 24. The behavior information calculated in this case 24 is information indicating the intensity of movement by the user 30, and has a strong correlation with the speed information 23.

The behavior information 24 according to the first embodiment is expressed in metabolic equivalents (METs) indicating exercise intensity. The individual identification module 11 calculates in Step S102 the behavior information 24 (METs) for every time point.

First, the individual identification module 11 acquires the acceleration x axis 2053, the acceleration y axis 2054, and the acceleration z axis 2055 from the activity level information table 205 in the sensor data 22, and calculates a scalar quantity S of triaxial acceleration in the x axis, the y axis, and the z axis. In this case, the scalar quantity S is calculated based on Expression (1), where the accelerations of respective axes are represented as xg, yg, and zg.

$$\text{Scalar quantity } S=(xg^2+yg^2+zg^2)^{(1/2)} \quad (1)$$

Next, the individual identification module 11 calculates the METs from the scalar quantity S based on Expression (2).

$$\text{METs}=a \times S+1 \quad (2)$$

In Expression (2), a is a constant. The METs value, which has a value of 1 at rest, namely, when the scalar quantity S is zero, indicates how many times greater the exercise intensity is from the value at rest.

The above-mentioned sensor data 22 includes triaxial acceleration. However, the sensor data 22 may include any measurement result, as long as the sensor data 22 is a result obtained by quantitatively measuring the intensity of movement by a person, such as heart rate, respiration rate, or amplitude. Further, the analysis module 10 according to this embodiment is capable of identifying an individual with greater accuracy from the tracks of a group by the individual identification module 11 calculating information such as respiration rate, heart rate, a walking or running pattern, or movement speed as the behavior information 24 based on those various pieces of sensor data 22.

FIG. 7 is an explanatory diagram for showing the behavior information 24 according to the first embodiment.

FIG. 7 is a diagram for showing a structural example of the behavior information 24 calculated based on the sensor data 22 in Step S102. The behavior information 24 includes a measurement date and time 241 and behavior information 242.

The measurement date and time 241 indicates the date and the time point at which the sensor data 22 is measured. The behavior information 242 indicates the behavior information calculated from the sensor data 22 measured at the date and time indicated by the measurement date and time 241. The behavior information 242 shown in FIG. 7 indicates METs.

One row indicates behavior information based on the sensor data 22 measured at one measurement date and time. One column indicates behavior information for one wearable device. As a result, the behavior information 24 includes behavior information 242 for each user ID. The sensor data 22 and the behavior information 24 has a feature that the user 30 is identified and the information is temporally sequential.

FIG. 8A, FIG. 8B, FIG. 8C, and FIG. 8D are explanatory diagrams for showing degree of similarity verification processing and association processing of the track information and the sensor data according to the first embodiment. FIG. 8E is a flowchart for illustrating the degree of similarity verification processing and association processing of the track information and the sensor data according to the first embodiment.

Figure 8:
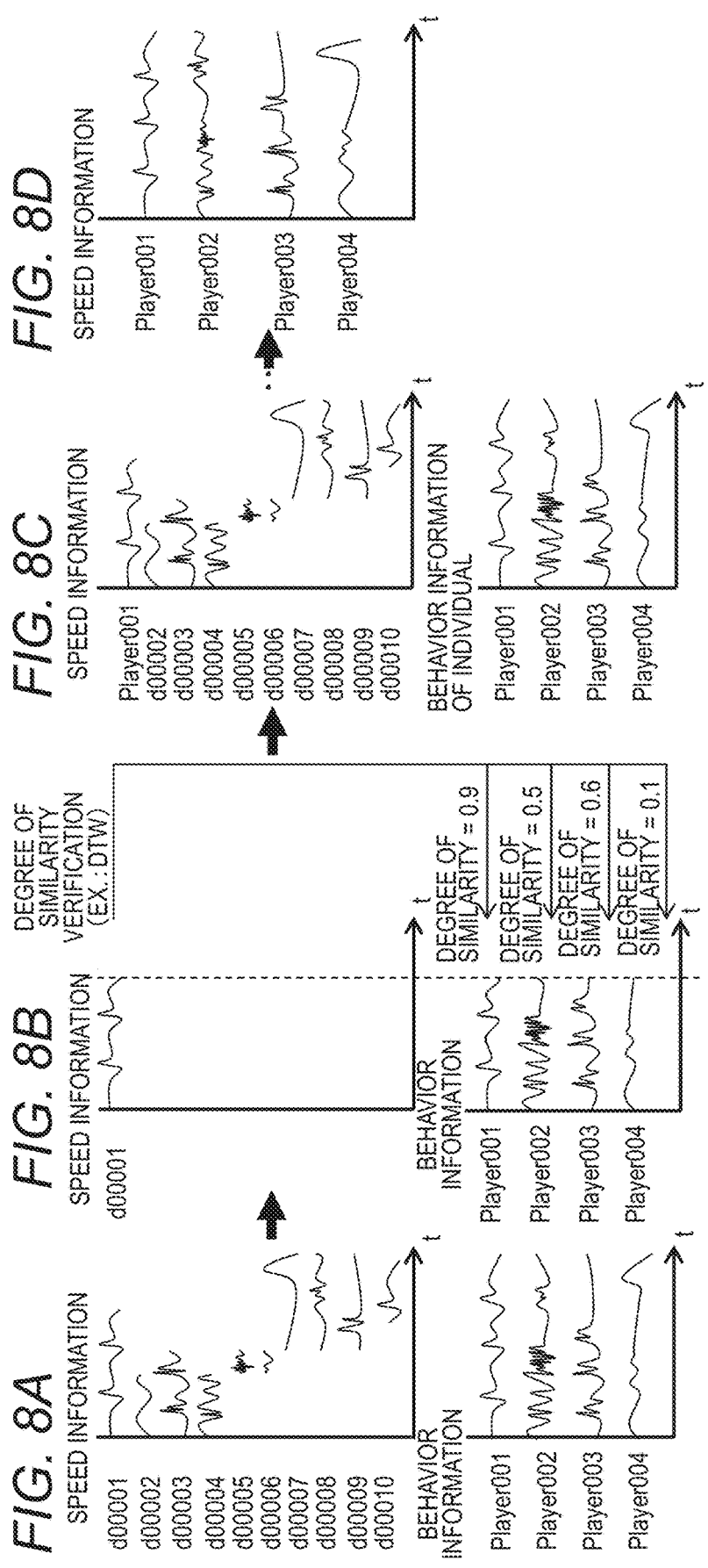
FIG. 8A is an explanatory diagram for showing degree of similarity verification processing and association processing of the track information and the sensor data according to the first embodiment.
FIG. 8B is an explanatory diagram for showing degree of similarity verification processing and association processing of the track information and the sensor data according to the first embodiment.
FIG. 8C is an explanatory diagram for showing degree of similarity verification processing and association processing of the track information and the sensor data according to the first embodiment.
FIG. 8D is an explanatory diagram for showing degree of similarity verification processing and association processing of the track information and the sensor data according to the first embodiment.
FIG. 8E is a flowchart for illustrating the degree of similarity verification processing and association processing of the track information and the sensor data according to the first embodiment.

In FIG. 8A, FIG. 8B, FIG. 8C, FIG. 8D, and FIG. 8E, the processing of Steps S103 and S104 is shown. FIG. 8A is an explanatory diagram for showing the speed information 23 and the behavior information 24, respectively, in graphs having a measurement date and time t on the horizontal axis.

Step S103 includes the following Step S1031 and Step S1032.

First, the individual identification module 11 selects the speed information 232 on one track (i.e., one column of the speed information 232 shown in FIG. 6) from the speed information 23 calculated in Step S101. Then, from among the plurality of pieces of behavior information 24 calculated in Step S102, the individual identification module 11 extracts behavior information 242 storing a value in the measurement date and time 241 that is the same as that in the measurement date and time 231 of the selected speed information 232 (i.e., a row of the behavior information 24 shown in FIG. 7) (S1031).

As a result, the behavior information 242 on the user 30 for which, during the period that the track information was being detected by the position detection apparatus 1, activity was measured by the wearable device 2, is identified.

In Step S1031, the individual identification module 11 selects the speed information on one track from the speed information 23 in descending order of a predetermined priority. In the following description, priority is higher when the data length is longer (the measurement date and time 241 was measured for a longer time, i.e., there are more rows in which speed is stored in the speed information 23).

Selecting speed information on a track having a longer data length allows the individual identification module 11 to compare speed information and behavior information that have been detected for a longer duration, and hence enables the tracks and the behavior information to be associated more accurately.

In FIG. 8B, a result is shown in which speed information on the track ID "d00001" having the longest measurement date and time 241 has been preferentially selected by the individual identification module 11. Further, results are also shown in which the behavior information on user IDs "Player 001", "Player 002", "Player 003", and "Player 004" has been extracted by the individual identification module 11.

The individual identification module 11 calculates a degree of similarity by executing a degree of similarity verification between the speed information on the track selected in Step S1031 and the behavior information extracted in Step S1031 (S1032). The individual identification module 11 calculates the degree of similarity by using known technology, such as dynamic time warping (DTW), for example, as the degree of similarity verification method.

The degree of similarity calculated in Step S1032 by the individual identification module 11 indicates whether or not a trend in the change of the values in time series of the speed information and a trend in the change of the values in time series of the behavior information are similar. In this embodiment, a larger value for the degree of similarity represents a greater similarity.

In FIG. 8B, the degree of similarity calculated based on the speed information on the track ID "d00001" and the extracted behavior information is shown.

Step S104 includes the following Steps S1041 and S1042.

The individual identification module 11 identifies the user ID of the behavior information having a degree of similarity calculated in Step S1032 that is equal to or more than a predetermined threshold b (b is a constant), and that is the largest degree of similarity. Then, the individual identification module 11 preferentially associates the identified user ID and the track ID of the speed information selected in Step S1031 (S1041).

The individual identification module 11 can remove track information on a user 30 who may be included in the group track information 21 measured by the laser radar but is not wearing the wearable device 2 by the individual identification module 11 using the threshold b set in advance to filter the behavior information. As a result, it is not necessary to associate the track ID of speed information having a smaller degree of similarity with the behavior information than the threshold b with the user ID of the behavior information.

In addition, in Step S1032, in at least any one of a case in which the distribution of a plurality of degrees of similarity calculated between the speed information on a selected one track and an extracted plurality of pieces of behavior information is small (i.e., when the calculated plurality of degrees of similarity are within a predetermined range), and, a case in which at least one degree of similarity that is about the same as the maximum degree of similarity has been calculated, in Step S1041, the individual identification module 11 returns to Step S1031 without associating the behavior information (user ID) with the selected speed information (track ID). Further, the individual identification module 11 selects the speed information having the next highest priority (e.g., the next longest data length) after the priority of the speed information used in the previous Step S1031.

This is performed because under such conditions, a plurality of pieces of behavior information that should be associated with the selected one track exist, and the likelihood that the behavior information to be associated can be correctly selected is low. As a result, by repeating Step S1031, tracks and behavior information that are more likely to correspond to each other are associated, which allows the individual identification module 11 to correctly associate the tracks and the behavior information.

Based on the processing described above, the individual identification module 11 can associate speed information and behavior information that are much more similar, which enables the accuracy of identifying the user 30 to be improved. It should be noted that after the individual identification module 11 has executed Steps S1032 and S1041 on the other pieces of speed information not selected in the speed information 23, the individual identification module 11 may also execute Steps S1032 and S1041 on the pieces of speed information not associated with behavior information.

In FIG. 8C, a result is shown in which speed information on the track ID "d00001" and behavior information on the user ID "Player 001" have been associated.

After Step S1041, when speed information that has not been assigned with behavior information is included in the speed information 23, the individual identification module 11 returns to Step S1031 and selects a piece of speed information having a lower priority than the speed information selected in the previous Step S1031.

It should be noted that in the second and subsequent iterations of Step S1031, when the measurement date and time of the selected speed information overlaps the measurement date and time of a piece of speed information that has already been associated with behavior information, it is not necessary for the individual identification module 11 to extract the behavior information that has already been associated.

For example, when speed information on the track ID "d00003" is selected after the behavior information on the user ID "Player 001" has been associated with the speed information on the track ID "d00001" in FIG. 8A, the speed information on the track ID "d00001" and the speed information on the track ID "d00003" have an overlapping measurement date and time. In this case, because there is one track to be associated with the behavior information on one individual at one timing (measurement date and time), the individual identification module 11 does not extract the user ID "Player 001".

As a result, the amount of behavior information for calculating the degree of similarity decreases, and hence the individual identification module 11 can improve the speed of the processing shown in FIG. 8A, FIG. 8B, FIG. 8C, and FIG. 8D, and improve the accuracy of identifying the user 30.

On the other hand, when the measurement date and time do not overlap, the individual identification module 11 may associate pieces of information having the same user ID but different track IDs. As a result, the individual identification module 11 can associate a plurality of pieces of speed information (track ID) not acquired sequentially with one piece of behavior information, which allows those plurality of pieces of speed information to be acquired as sequential speed information.

After the processing of Step S1031 to Step S1041 has been executed on all of the pieces of speed information included in the speed information 23, the individual identification module 11 outputs information indicating an association between the track ID indicated by the speed information 23 and the user ID indicated by the behavior information 24 (S1042).

In FIG. 8D, a result is shown in which the track ID and the user ID have been associated. In Step S1042, the individual identification module 11 outputs information (individual identification information 25) such as that shown in FIG. 8D.

Figure 9:
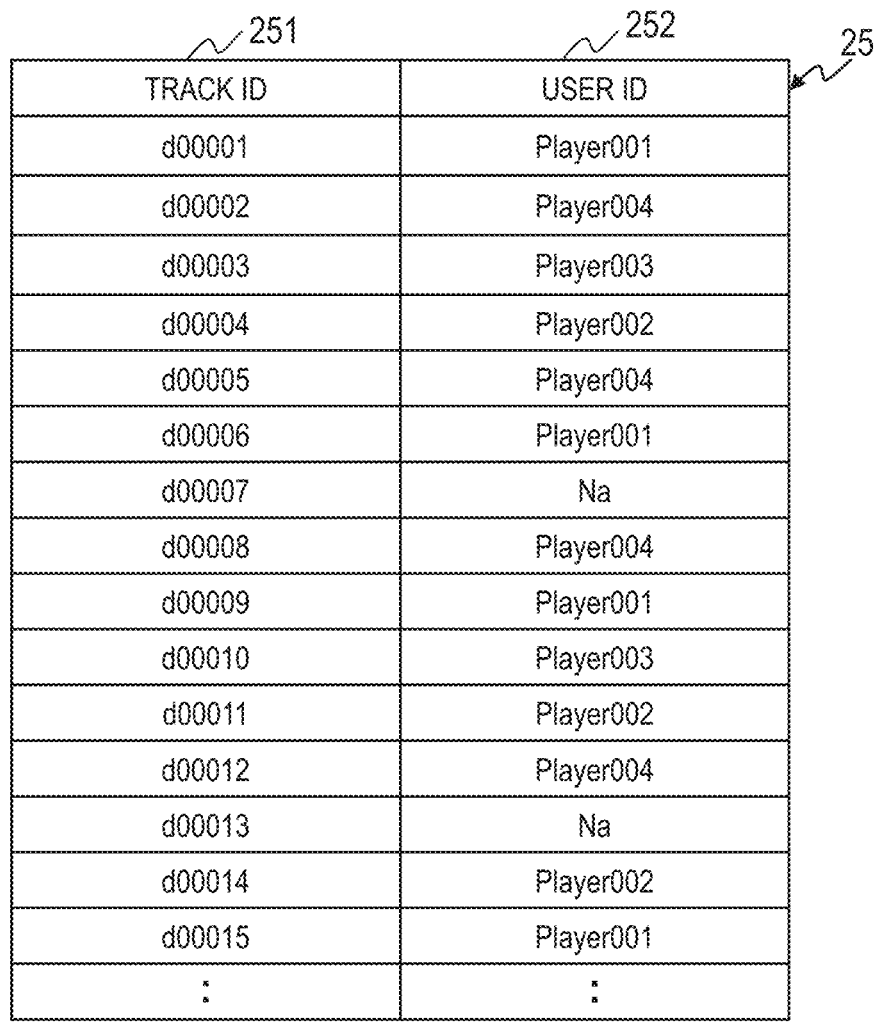
FIG. 9 is an explanatory diagram for showing the individual identification information according to the first embodiment.

FIG. 9 is an explanatory diagram for showing the individual identification information 25 according to the first embodiment.

The individual identification module 11 is configured to output the result obtained in Step S1042 as the individual identification information 25 such as that shown in FIG. 9. The individual identification information 25 includes a track ID 251 and a user ID 252. The track ID 251 corresponds to the track ID of the speed information 23. The user ID 252 corresponds to the user ID of the behavior information 24.

In the individual identification information 25, one row indicates the user ID associated with one track ID. In Step S104, a symbol "Na" is stored in the user ID column for track IDs of speed information that have not been associated with a user ID of the behavior information, such as when the degree of similarity is less than the threshold b, for example.

Figure 10A:
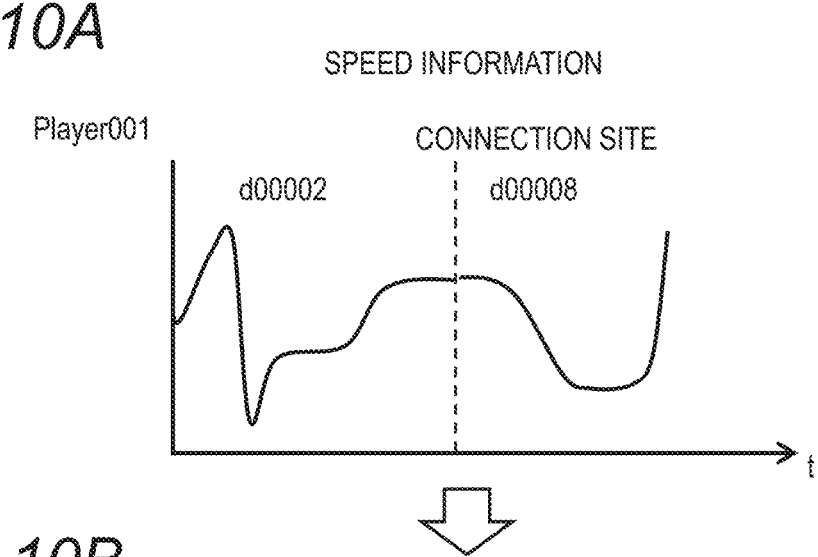
FIG. 10A is an explanatory diagram for showing evaluation processing by a track connecting module according to the first embodiment.
Figure 10B:
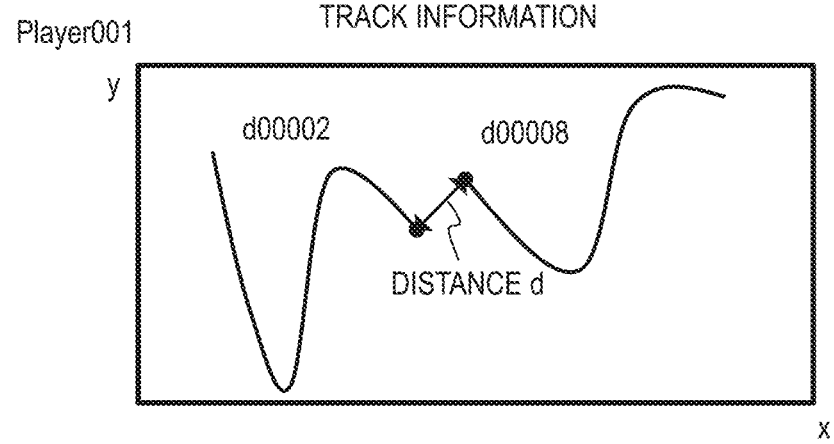
FIG. 10B is an explanatory diagram for showing evaluation processing by a track connecting module according to the first embodiment.

FIG. 10A and FIG. 10B are explanatory diagrams for showing evaluation processing by a track connecting module according to the first embodiment.

The graphs shown in FIG. 10A and FIG. 10B are conceptual drawings of the evaluation processing performed in Step S106.

In Step S105, the track generation module 12 selects one user ID from the individual identification information 25, and identifies at least one track ID associated with the selected user ID. Further, the track generation module 12 generates individual track information 26 on one user 30 by arranging the specified track IDs in time series based on the measurement date and time 231 of the speed information 23. In this case, the behavior information on the selected user ID is denoted as behavior information A.

In FIG. 10A, speed information arranged in time series based on the track information on one user 30 is shown.

In addition, in Step S106, the track generation module 12 identifies a connecting portion of the track included in the individual track information generated in Step S105. The connecting portion is from the measurement date and time at which the speed information on the one track ID finishes (hereinafter referred to as the "finish point") to the measurement date and time at which another track first starts after the finish point (hereinafter referred to as the "start point"). In this case, the track including the finish point is denoted as track B, and the track including the start point is denoted as track C.

The connecting portion in FIG. 10A is the portion between the measurement date and time of the speed information having the track IDs "d00002" and "d00008".

Further, the track generation module 12 is configured to acquire the position of the finish point of the track B (x coordinate 2033 and y coordinate 2034) and the position of the start point of the track C (x coordinate 2033 and y coordinate 2034) from the track information table 203. Then, the track generation module 12 calculates a distance d between the position of the finish point of the track B and the position of the start point of the track C.

FIG. 10B is an explanatory diagram for showing the distance d between two tracks. In FIG. 10B, the positions of two tracks, and the distance d between the finish point of the track having the track ID "d00002" and the start point of the track having the track ID "d00008" are shown.

Further, the track generation module 12 is configured to evaluate the distance d of the connecting portion. Specifically, the track generation module 12 determines whether or not the distance d of the connecting portion is equal to or more than a threshold c (c is a constant), and when it is determined that the distance d is equal to or more than the threshold c, the track generation module 12 evaluates that the track associated with the behavior information A is not suitable. Then, the track generation module 12 controls the individual identification module 11 to again execute Step S104.

It should be noted that the track generation module 12 may also evaluate that the track associated with the behavior information A is not suitable when an estimated speed at the connecting portion, which is calculated based on the distance d, the measurement date and time of the finish point, and the measurement date and time of the start point, is determined as being very fast, and hence not reasonable, in view of the characteristics of the user 30.

After Step S106 performed by the track generation module 12, the individual identification module 11 associates the track ID of the track C positioned later in the time series and the user ID of behavior information having a calculated degree of similarity that is equal to or more than the threshold b, and, has the next largest degree of similarity. As a result, a behavior index associated with the track C is changed. In this case, the degree of similarity is the degree of similarity calculated in Step S1032 between the speed information on the track C and the behavior information extracted in Step S1031.

Further, the behavior information having the next largest degree of similarity is, among the pieces of behavior information for which a degree of similarity with the speed information on the track C has been calculated, a piece of behavior information having a degree of similarity that is lower than the degree of similarity calculated between the behavior information A and the speed information on the track C, and, has the next largest degree of similarity to that degree of similarity.

In addition, in this processing as well, the individual identification module 11 does not associate behavior information and the track C having a degree of similarity that is smaller than the threshold b. Still further, when the behavior information having the next largest degree of similarity is already associated with the track ID of another track at the measurement date and time of the track C, the individual identification module 11 may associate the user ID of behavior information having an even lower degree of similarity and the track ID of the speed information on the track C.

Further, in this embodiment, the individual identification module 11 is configured to change, when it has been evaluated that the track associated with the behavior information A is not suitable, the behavior information to be associated with the track C having a later measurement date and time. However, the individual identification module 11 may also be configured to change the behavior information to be associated with the track B having an earlier the measurement date and time.

Repeating the processing of Step S106, in which, based on the distance d between a plurality of tracks, it is determined that the track associated with the behavior information is not suitable, and the processing of Step S104, in which the behavior information associated with the track is changed, enables the behavior information to be associated with a suitable track, and thus the track and the behavior information on the user 30 to be correctly associated.

Further, in Step S104, the individual identification module 11 can determine the behavior information to be associated with the track C in descending order of likelihood of being similar, by changing the behavior information associated with the track C to the behavior information having the next largest degree of similarity. As a result, the track and the behavior information on the user 30 can be associated more correctly.

After Step S1041, the individual identification module 11 executes Step S1042, and finishes Step S104.

It should be noted that when three or more tracks are associated with the behavior information A, the track generation module 12 may calculate the distance d for all of the connecting portions, determine the tracks for which the behavior information to be associated is to be changed, and then execute Step S104 on the tracks to be changed.

The track generation module 12 repeats Steps S105, S106, and S104 until the distance between the finish point and the start point of the connecting portion between the tracks is smaller than the threshold c. Repeating those processing steps enables suitable tracks to be associated with the behavior information A on the user 30, and accurate individual track information 26 to be generated.

After the evaluation processing has finished, the track generation module 12 stores the generated individual track information 26 in the DB 20. As a result of executing Step S106, the individual track information 26 can be accurately generated.

FIG. 11 is an explanatory diagram for showing the individual track information 26 generated by the track generation module 12 according to the first embodiment.

The individual track information 26 includes one table for each sensor ID. In individual track information 26, one row indicates the position coordinates of the track at one measurement date and time. In this case, the position coordinates are position information (x coordinate and y coordinate) defined by the spatial reference system WGS 84, and correspond to the x coordinate 2033 and the y coordinate 2034 in the track information table 203.

The individual track information 26 has a feature that the user 30 is identified and the information is temporally sequential (i.e., a value is stored for each measurement date and time).

Figure 12:
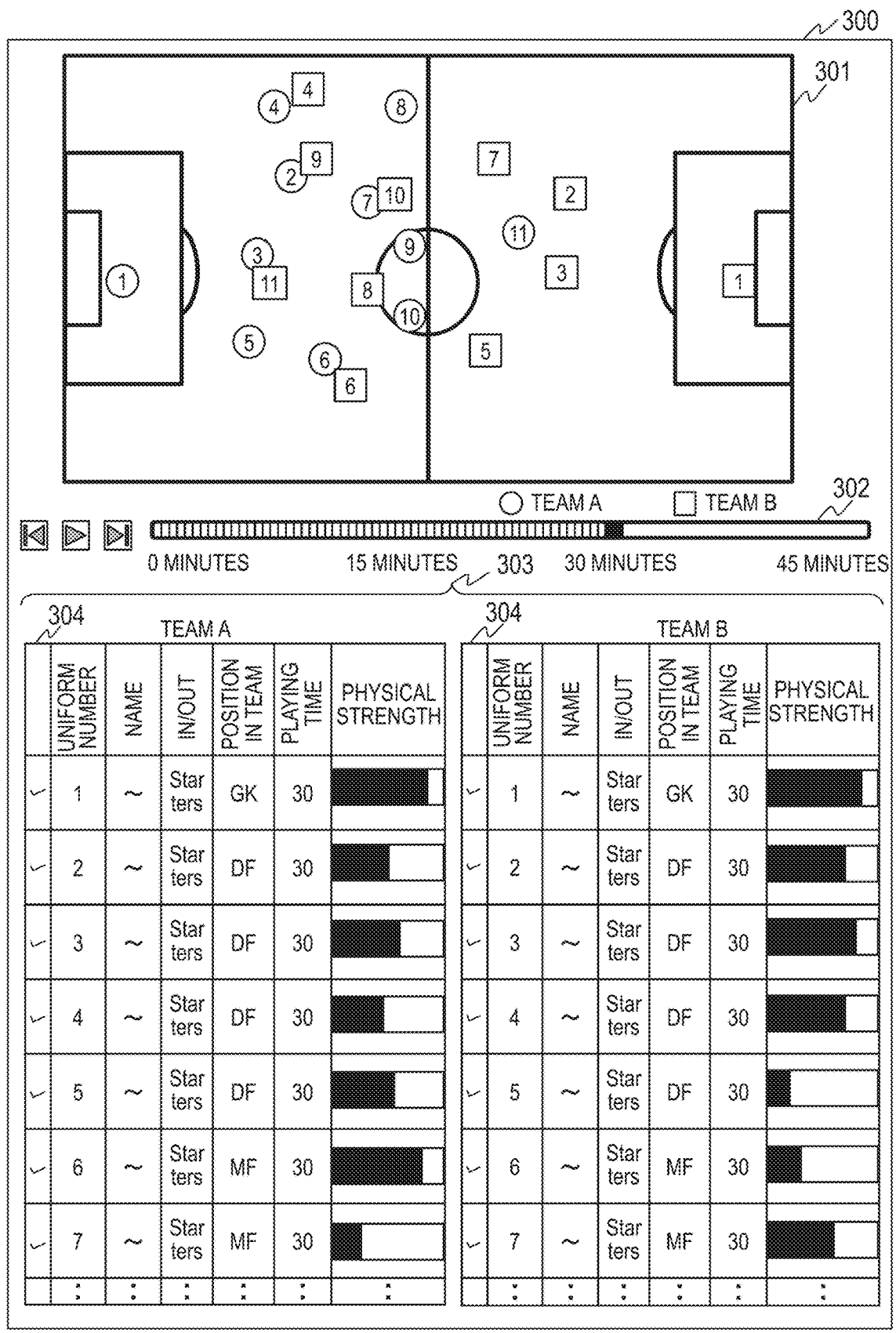
FIG. 12 is an explanatory diagram for showing a screen generated by the display module according to the first embodiment.

FIG. 12 is an explanatory diagram for showing a screen 300 generated by the display module 13 according to the first embodiment.

The screen 300 shown in FIG. 12 is a screen for monitoring the tracks of the players appearing in a soccer match.

The display module 13 is configured to generate the screen 300 in a manner that allows the screen 300 to recreate the tracks of each player (user) during the game, by referring to the individual track information 26, the user information table 204, and the area table 201, and the like. The screen 300 shown in FIG. 12 includes images 301, 302, and 303.

The image 301 displays the tracks of each player (user) on the soccer field based on the individual track information 26. Further, the display module 13 is configured to change, based on the user type 2043 of each player, a graphic representing the tracks of the users 30 for each team and to display the uniform number of the users 30 (players) included in the graphic representing the tracks of the users 30.

As a result, because the display module 13 is configured to generate a screen 300 that additionally displays information for distinguishing the users 30 in the tracks detected by the position detection apparatus 1, information indicating the movements and tracks (position in time series) of the users 30 performing the athletic activity can be correctly presented to the operator.

The image 302 is a timeline. The image 302 corresponds to the measurement date and time of the individual track information 26. The display module 13 is configured to receive, when an operation is performed on the timeline of the image 302, a measurement date and time from the image 302, and display in the image 301 a graphic indicating the player based on the position coordinates of an arbitrary measurement date and time.

In addition, when the user information table 204 stores various types of information, such as the team that the user belongs to, uniform number, and the user's role (position) in the team, as the user type 2043 corresponding to the user ID 2041, the display module 13 is configured to display information identified by the user IDs in the image 303 as information on the players belonging to the team. Further, the display module 13 is capable of receiving operations made in the image 304, and selecting the players for which a track is to be displayed in the image 301 by receiving the users selected by those operations.

Further, when the activity level information table 205 in the sensor data 22 includes an arm movement amount, the display module 13 is capable of estimating in time series a unique pitch or stride angle of the walking or running of each player based on the sensor data 22 to estimate the level of fatigue based on the estimated unique pitch or stride angle. This allows a remaining physical strength to be estimated for each measurement date and time.

In addition, the display module 13 is capable of displaying the remaining physical strength during a match at the measurement date and time specified by the timeline in the image 302. Similarly, for example, a balance and quality of running may be estimated by using sensor data 22 in which the arm movement amount has been measured. As a result, such information can be additionally displayed.

Further, the display module 13 may also be configured to calculate a playing time by subtracting the start time from the finish time of the measurement date and time of the behavior information on the user, and display the calculated playing time in the image 303.

Figure 13:
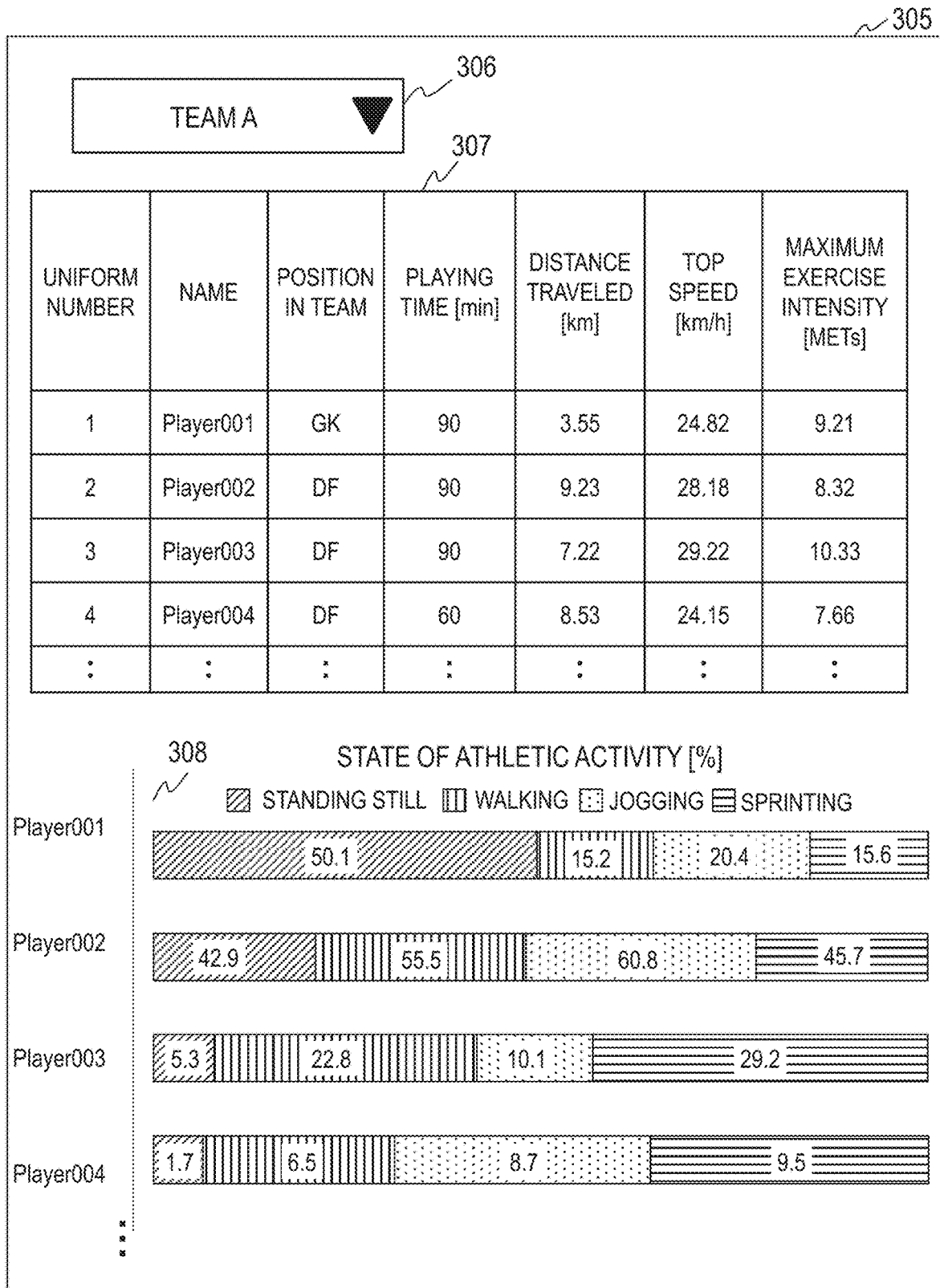
FIG. 13 is an explanatory diagram for showing a screen generated based on the speed information according to the first embodiment.

FIG. 13 is an explanatory diagram for showing a screen 400 generated based on the speed information 23 according to the first embodiment.

The screen 400 shown in FIG. 13 is a screen for displaying a result obtained by analyzing the performance of a player who has appeared in the soccer match. The display module 13 is configured to determine and display the performance of the players appearing in the soccer match by using the individual track information 26, the user information table 204, the area table 201, the speed information 23, the behavior information 24, and the like.

The screen 400 includes images 306, 307, and 308. The image 306 is a region that allows the operator to select the team name by a tab. The display module 13 is configured to identify a user ID indicated by the user type 2043 as having the team name input using the image 306, and display the performance of the player corresponding to the identified user ID in the images 307 and 308.

The display module 13 is configured to determine performance information to be displayed in the images 307 and 308 based on the activity level information table 205 including the identified user ID in a user ID 2051.

The image 307 displays, as the performance information, a distance traveled, a top speed, the number of sprints, a maximum exercise intensity, and the like, as well as various types of other information on each player. Further, the image 308 displays, as the performance information, respective proportions of standing still, walking, jogging, and sprinting of each player. Therefore, the operator can use the screen 305 shown in FIG. 13 to confirm the performance of each player during a match, and to compare performance among players.

Figure 14:
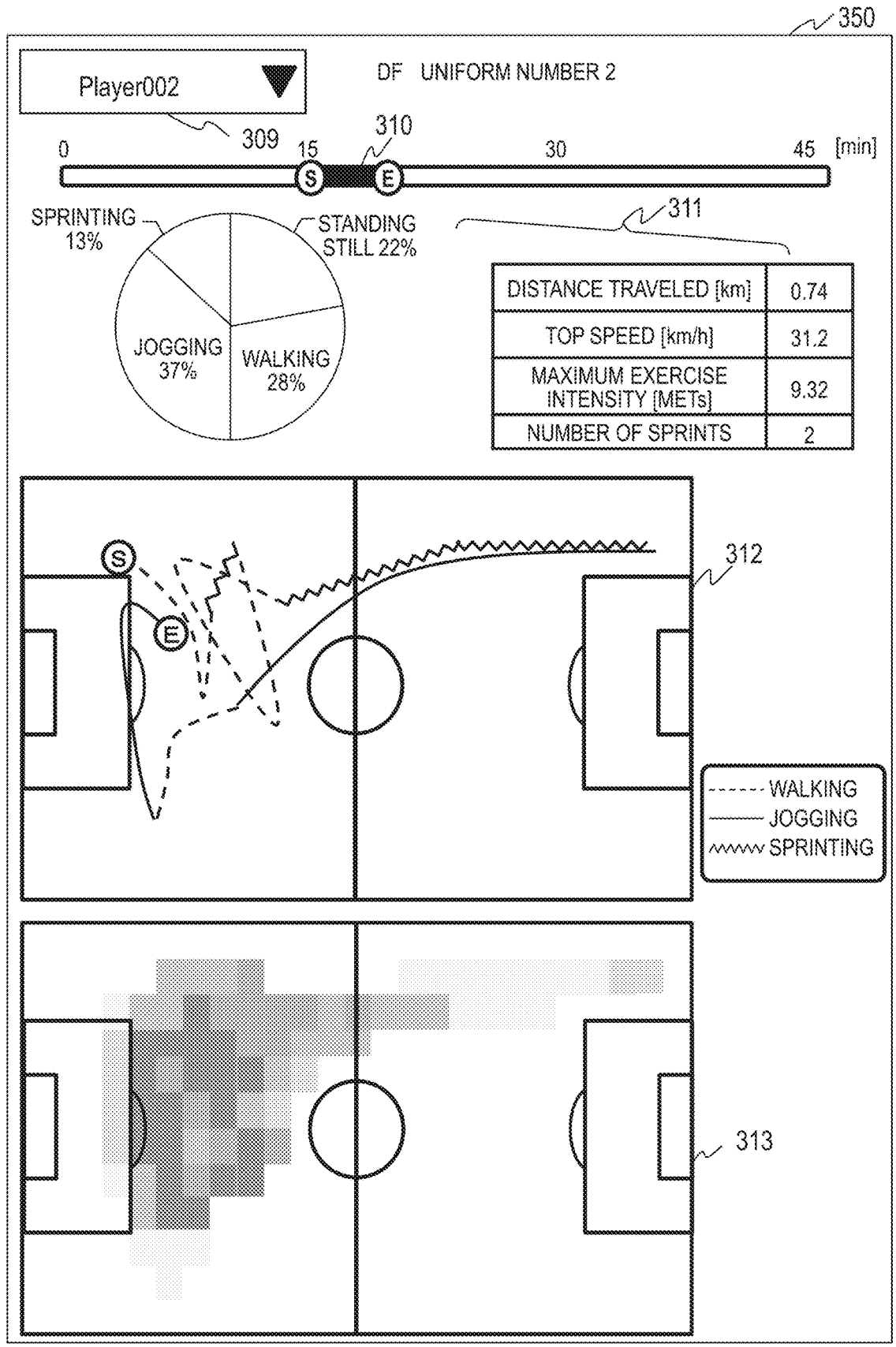
FIG. 14 is an explanatory diagram for showing another screen generated based on the speed information according to the first embodiment.

FIG. 14 is an explanatory diagram for showing another screen 350 generated based on the speed information 23 according to the first embodiment.

The screen 350 is for displaying a track of one player in a soccer match, and, a result of performance analysis.

The display module 13 is configured to generate, and display on the screen 350, a recreation of the tracks of a specified player and a result of performance analysis, by using the individual track information 26, the user information table 204, the area table 201, the speed information 23, the behavior information 24, and the like.

The screen 350 includes images 309, 310, 311, 312, and 313. The image 309 is a region that allows the operator to select by a tab the player the operator wishes to refer to.

The image 310 is a timeline of the measurement date and time. The operator may select a performance time band that he or she wishes to refer to by specifying the start time point and the finish time point in the image 310.

The display module 13 is configured to receive the time band selected in the image 310, and display the respective proportions of standing still, walking, jogging, and sprinting, the number of sprints, the maximum exercise intensity, and the like, in the time band selected in the image 310. Further, other information than this may also be displayed in the image 311.

The display module 13 may be configured to identify whether or not the track at each measurement date and time is of a player standing still, walking, jogging, or sprinting, based on the speed indicated by the speed information 23. Further, based on the position information indicated by the track information table 203 of the track associated with the player, the display module 13 may also be configured to calculate a movement distance during the selected time band as the distance traveled.

The image 312 displays the track of the time band selected in the image 310 by using lines that allow walking, jogging, sprinting, and the like to be distinguished from each other.

The image 313 shows a heat map of the players in the time band selected in the image 310. Displaying the image 313 allows the locations at which the players have been active to be displayed.

Further, the display module 13 is configured to change a depth of color to display a difference in the active time per unit area in the image 313. In this case, portions having a deeper coloring indicate a position having a longer time for which the players have been active.

Therefore, the operator can confirm the tracks of the individual players during the match, and confirm the performance of the players in detail, by referring to the image 313.

Figure 15:
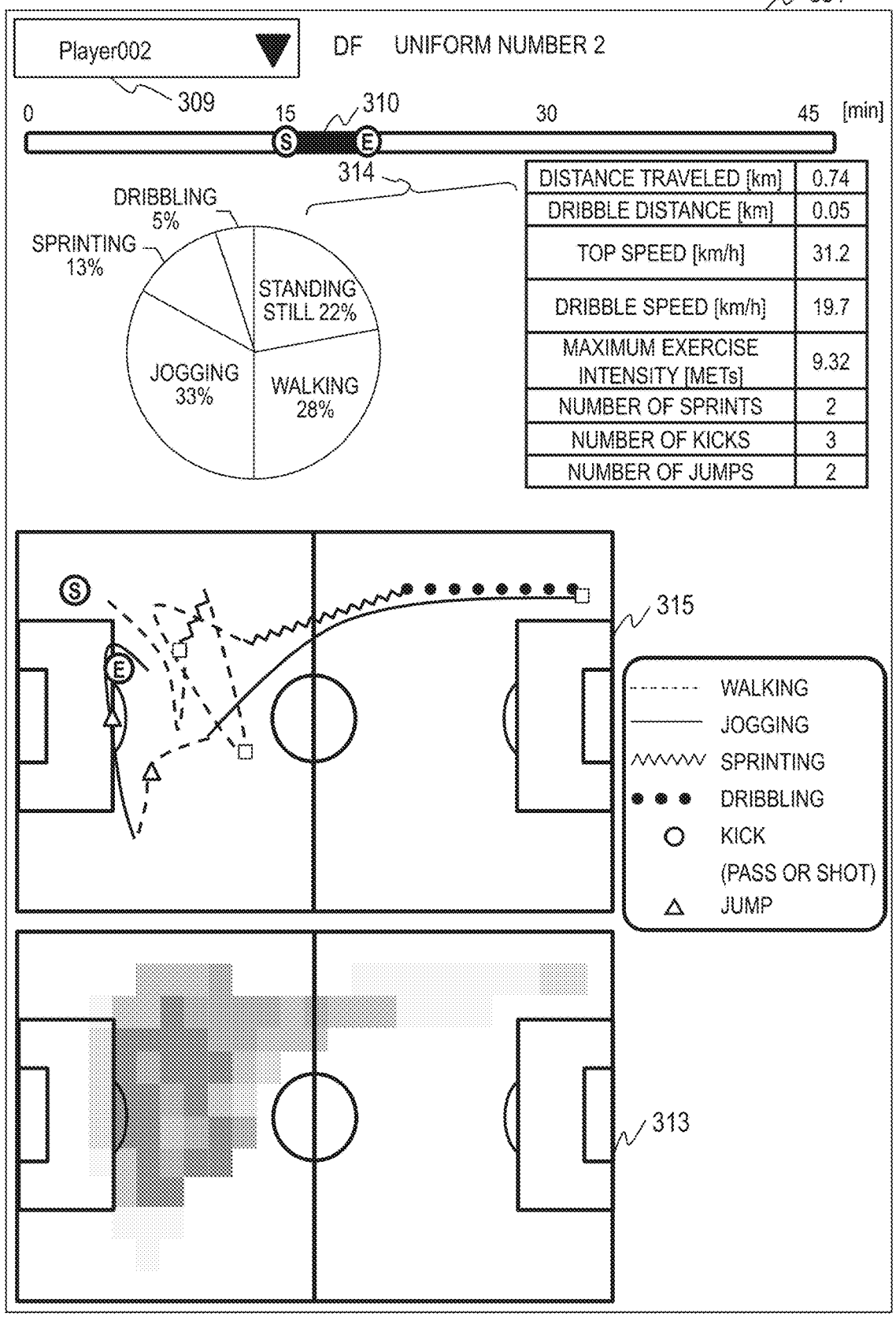
FIG. 15 is an explanatory diagram for showing a screen generated based on impact intensity according to the first embodiment.

FIG. 15 is an explanatory diagram for showing a screen 351 generated based on impact intensity according to the first embodiment.

In the example described above, a wearable device 2 including a triaxial acceleration sensor is worn around the wrist. However, the user may also wear the wearable device 2 on his or her feet, or embed the wearable device 2 in his or her shoes. Further, such a wearable device 2 may be configured to add to the sensor data a measurement result indicating an intensity and direction of a shock received by the leg.

As a result, the display module 13 can detect kicking, dribbling, and jumping based on the intensity and direction of the shock indicated by the sensor data 22.

The screen 351 shown in FIG. 15 is an example of a screen displaying a detection result of kicking, dribbling, jumping, and the like, on the screen 350 shown in FIG. 14. The screen 351 includes images 309, 310, 314, 315, and 313. The images 309, 310, and 313 shown in FIG. 15 are the same as the images 309, 310, and 313 shown in FIG. 14.

The image 314 displays, in addition to the content of the image 311 shown in FIG. 14, a dribbling ratio, a dribbling distance, a dribbling speed, the number of kicks, and the number of jumps.

Further, the image 315 displays the tracks in the time band selected in the image 310 by using lines that allow walking, jogging, sprinting, dribbling, kicking, jumping, and the like to be distinguished from each other. In addition, because a kick strength, a contact point, and the like can be estimated, the display module 13 may additionally display those pieces of information in the image 315.

Still further, the analysis module 10 according to this embodiment may additionally include a sensor mounted in the worn wearable device 2, thereby enabling the state and actions of various players to be measured. Those measurement results may be associated with the track information.

For example, the heart rate and the pulse rate of the user 30 may be measured by mounting a heart rate sensor and a pulse sensor in the wearable device 2, which enables the display module 13 to associate and display changes in the heart rate and the pulse rate with the displayed tracks. As a result, the operator can obtain an index for evaluating an exercise load level and fatigue.

Further, altitude may be measured by mounting an air pressure sensor in the wearable device 2. In this case, for games in which a jumping action is a frequent and important action, such as basketball, volleyball, and handball, the display module 13 may be configured to associate and display information indicating the quality of a jump with the displayed tracks.

In addition, when the user 30 is wearing on a plurality of places of his or her body, such as on the trunk and the four limbs, wearable devices 2 including an acceleration sensor and a gyro sensor, the display module 13 may be configured to recreate a body orientation in a three-dimensional (3D) model. As a result, in addition to the track information, the display module 13 can recreate and display the movements during exercise in detail.

In addition to the examples described above, a performance and a state suitable for various games and situations may be measured and displayed together with the track information by selecting the combination of the types of sensors to be mounted in the wearable device 2, and changing the place and the number of the wearable devices 2 that are worn.

Second Embodiment

Figure 16:
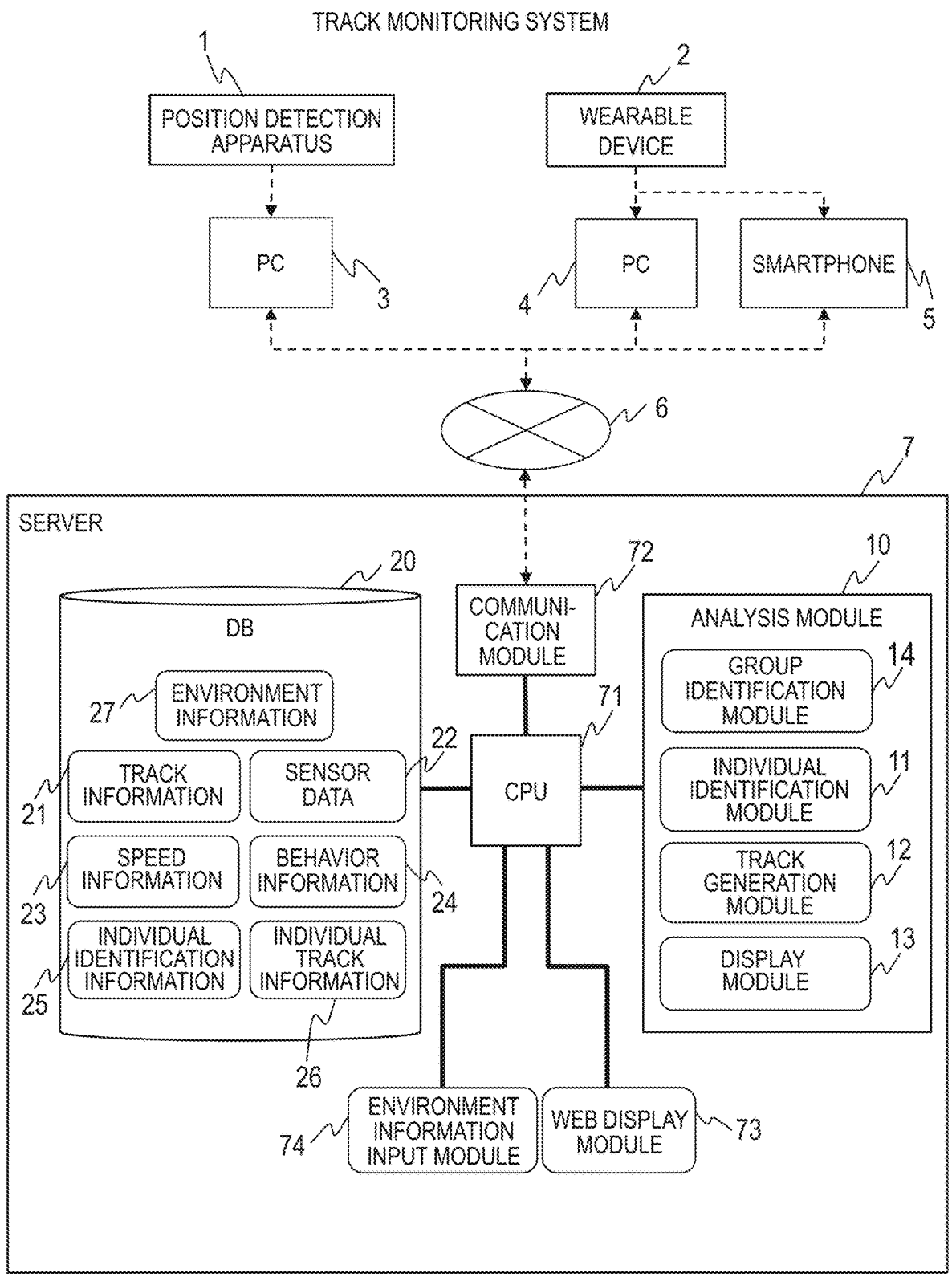
FIG. 16 is a block diagram for illustrating a configuration of a track monitoring system according to a second embodiment of this invention.

FIG. 16 is a block diagram for illustrating a configuration of a track monitoring system according to a second embodiment of this invention.

The track monitoring system according to the second embodiment includes, as in the track monitoring system according to the first embodiment, a position detection apparatus 1, a wearable device 2, a PC 3, a PC 4, a smartphone 5, a network 6, and a server 7.

Differences between the track monitoring system according to the second embodiment and the track monitoring system according to the first embodiment are now described. The analysis module 10 according to the second embodiment is different from the analysis module 10 according to the first embodiment in including a group identification module 14. The DB 20 according to the second embodiment is different from the DB 20 according to the first embodiment in including environment information (identification information) 27. The server 7 according to the second embodiment is different from the server 7 according to the first embodiment in including an environment information input module 74. In other points, the track monitoring system according to the second embodiment and the track monitoring system according to the first embodiment are the same.

As a result of the above-mentioned differences between the second embodiment and the first embodiment, in the second embodiment, the operator can quickly refer to a large amount of track information 21 and sensor data 22 that is accumulated in the DB 20.

The environment information input module 74 is configured to display an environment display input screen on an output apparatus, such as the PC 3, the PC 4, and the smartphone 5, and receive environment information input by the operator. Further, the environment information input module 74 is configured to store the input environment information in the environment information 27.

The environment information according to this embodiment indicates information on the athletic activity of the users 30, and includes information for identifying the track information 21 and the sensor data 22 based on the athletic activity. For example, the environment information indicates the content of the athletic activity, the time and location at which the athletic activity is performed, the participants in the athletic activity, and the like. The analysis module 10 according to the second embodiment is capable of identifying a candidate for the track information 21 and a candidate for the sensor data 22 to be associated based on the environment information 27.

The analysis module 10 is capable of performing data analysis on the athletic activity in a short period of time by referring to the environment information 27. Further, the analysis module 10 is capable of extracting tracks and movements from an athletic activity, such as training, in which various practice menus are performed in a short period of time while replacing the participating members.

For example, for track monitoring during an athletic activity according to the second embodiment, the sensor data 22 collected from a constantly-worn wearable device 2 and the track information 21 measured under various environments, such as during daily training and during matches, are accumulated in the database 20.

The group identification module 14 is configured to select from the DB 20 the group track information 21 on a specific location obtained by the position detection apparatus 1 and the sensor data 22 of the participants included in the group, by using the environment information 27, which defines a time period, location, participants, and the like. Then, based on the same procedure as in the first embodiment, the individual identification module 11, the track generation module 12, and the display module 13 detect and display the tracks and the movements of the individuals.

It should be noted that the group identification module 14 may be realized by one program or integrated circuit, or by a plurality of programs or a plurality of integrated circuits for each process to be executed.

FIG. 17 is an explanatory diagram for showing a screen 352 displayed by the environment information input module 74 according to the second embodiment.

The screen 352 includes an environment information input page 316, a participant selection page 319, and a grouping selection page 320. The environment information input page 316 is for inputting the name, the start time point, and the finish time point of the athletic activity, the area name of the area at which the athletic activity is performed, the participants in the athletic activity, and a grouping 318 of the participants.

The environment information input page 316 is a screen example for inputting environment information on the athletic activity that the operator wishes to analyze. The operator inputs the activity name, the start time point, the finish time point, and the like in each row of the environment information input page 316. Further, the operator uses a tab to select the area name of the area at which the activity is performed from among candidate areas registered in advance. In addition, the operator inputs the participants in the participant 317.

When all of the people wearing the wearable device 2 and registered in advance are participants, the operator places a check mark in the all check box. Further, when the operator is to select the participants, the operator selects the "individual selection" check box of the participant 317.

The environment information input module 74 is configured to display, when the "individual selection" of the participant 317 has been selected, the participant selection page 319. The participant selection page 319 is a screen for displaying a list of the users 30 who have been registered in advance and are wearing the wearable device 2 to allow the operator to select the participants.

The grouping 318 is configured to display an interface that lets the operator select a grouping of the participants. When the operator does not need to group the participants, the operator places a check mark in the "none" check box. Further, when the participants are to be grouped, the operator selects "advanced settings".

The environment information input module 74 is configured to display, when the "advanced settings" of the grouping 318 has been selected, the grouping selection page 320. The grouping selection page 320 is for displaying a list of the users 30 who have been registered in advance and are wearing the wearable device 2. Further, the grouping selection page 320 is for displaying an interface that lets the operator select the team of the users 30.

Further, in this embodiment, the users 30 are grouped based on the team to which the users 30 belong. However, this invention is not limited to this. The users 30 may be grouped based on their role (position) in the team, school grade, and the like. In addition, the users may also be grouped by using various types of information registered in the user information table 204.

The environment information received by the environment information input module 74 is stored in the environment information 27 of the database 20. Further, the environment information input module 74 may be configured to store in the user type 2043 of the user information table 204 a grouping of the users 30 input via the grouping selection page 320.

FIG. 18 is an explanatory diagram for showing the environment information 27 according to the second embodiment.

The environment information 27 includes an activity information table 206 for recording information on an activity for which the track information 21 was measured, and an environment information table 207 in which the activity time period, location, environment in which the participants performed the activity, and the like are recorded for each activity ID in order to identify the group that performed the activity.

The activity information table 206 includes an activity ID 2061 and an activity name 2062. The activity ID 2061 records the ID set for each athletic activity in order to recognize the athletic activity for which the track information 21 was measured. The activity ID 2061 may be the same as the activity ID input on the environment information input page 316, or may be an ID assigned based on that activity ID.

The activity name 2062 records the name of the athletic activity for which the track information 21 was measured. As a result, the Web display module 73 can display a screen for showing the area name. The activity name 2062 stores the activity name input on the environment information input page 316.

The environment information table 207 includes an activity ID 2071, a start time point 2072, a finish time point 2073, an area ID 2074, and a user ID 2075. The activity ID 2071 corresponds to the activity ID 2061. The start time point 2072 and the finish time point 2073 indicate the start time point and the finish time point of the athletic activity indicated by the activity ID 2071. The start time point 2072 and the finish time point 2073 store the start time point and the finish time point input on the environment information input page 316.

The area ID 2074 indicates the location at which the athletic activity indicated by the activity ID 2071 was performed. The area ID 2074 stores the ID assigned to the area name input on the environment information input page 316. The user ID 2075 stores the user ID of the users who were participants in the athletic activity indicated by the activity ID 2071, and, who were wearing the wearable device 2.

Figure 19:
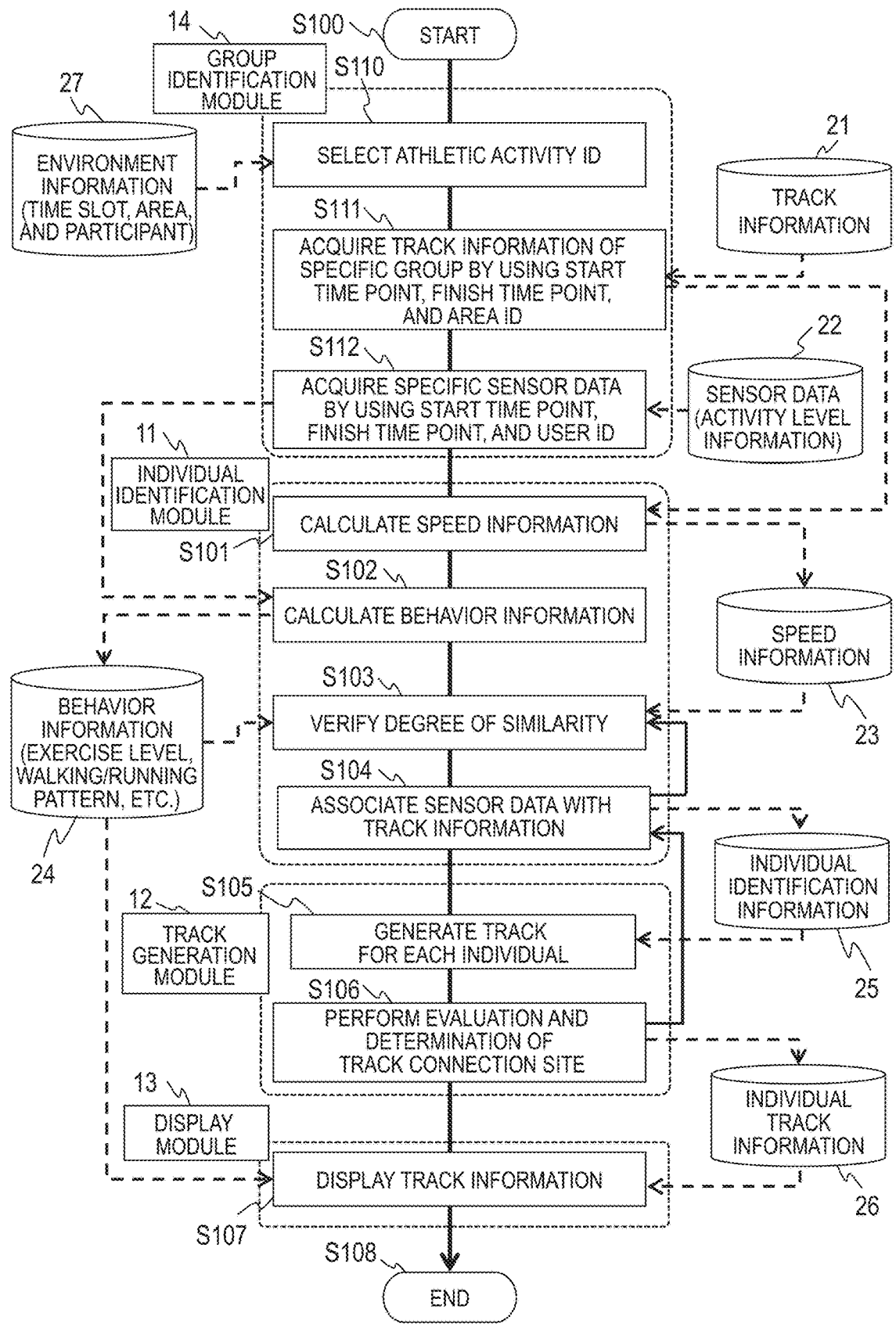
FIG. 19 is a flowchart for illustrating processing performed by the analysis module according to the second embodiment.

FIG. 19 is a flowchart for illustrating processing performed by the analysis module 10 according to the second embodiment.

The group identification module 14 selects from the activity information table 206 the activity ID 2061 of the athletic activity for which the tracks of the individuals are to be analyzed (S110). In this case, the group identification module 14 may execute the processing illustrated in FIG. 19 by repeating the processing for all of the activity IDs 2061, or may execute the processing illustrated in FIG. 19 for an athletic activity selected by a screen 353 that is described later or the like.

Further, the group identification module 14 identifies an entry in the environment information table 207 that includes the activity ID selected in Step S110 in the activity ID 2071. In addition, the group identification module 14 refers to the start time point 2072, the finish time point 2073, and the area ID 2074 of the identified entry, and acquires from the track information 21 the track information of a specific group (S111).

Specifically, the group identification module 14 acquires the track ID of an entry in the track information table 203 whose measurement date and time 2032 is between the start time point 2072 and the finish time point 2073 of the identified entry, and, in which the area ID 2074 of the identified entry and the area ID 2035 are the same.

Further, the group identification module 14 identifies the entry in the track line table 202 in which the acquired track ID is included in the track ID 2021, and identifies the entry in the area table 201 having the same area ID 2011 as the area ID 2074. By acquiring those identified entries, the group track information corresponding to the selected activity ID is acquired.

In addition, the group identification module 14 identifies the sensor data of the user 30 corresponding to the start time point 2072, the finish time point 2073, and the user ID 2075 in the environment information table 207 of the activity ID selected in Step S110 by referring to the user ID 2051 and the measurement date and time 2052 of the sensor data 22.

By acquiring the identified entry, the sensor data corresponding to the selected activity ID is acquired (S112).

After Step S112, the individual identification module 11 and the track generation module 12 execute Steps S101 to S106 illustrated in FIG. 5 on the group track information acquired by the group identification module 14 and the identified sensor data, to thereby associate the identified tracks and the identified users and generate the individual track information 26. Further, the display module 13 displays the tracks and the movements of the individuals on a screen.

It should be noted that by selecting the activity ID 2061 in Step S110, the group identification module 14 identifies the measurement date and time 2032 and the area ID 2035 of the track information table 203, and the user ID 2051 and the measurement date and time 2052 of the activity level information table 205. However, when an instruction, such as the user type 2043, has been received via the Web display module 73, the group identification module 14 may also identify the sensor data based on the instructed content.

By performing the processing described above, the analysis module 10 can associate tracks and the behavior information on the users 30 based on the tracks detected under arbitrary conditions (measurement date and time, area ID, etc.), and, sensor data on the users 30 of arbitrary conditions (measurement date and time, user ID, etc.). As a result, a part of the track information 21 and a part of the sensor data 22 are associated, which allows processing speed to be improved, enabling the operator to quickly refer to the correspondence between the tracks and the users 30.

Figure 20:
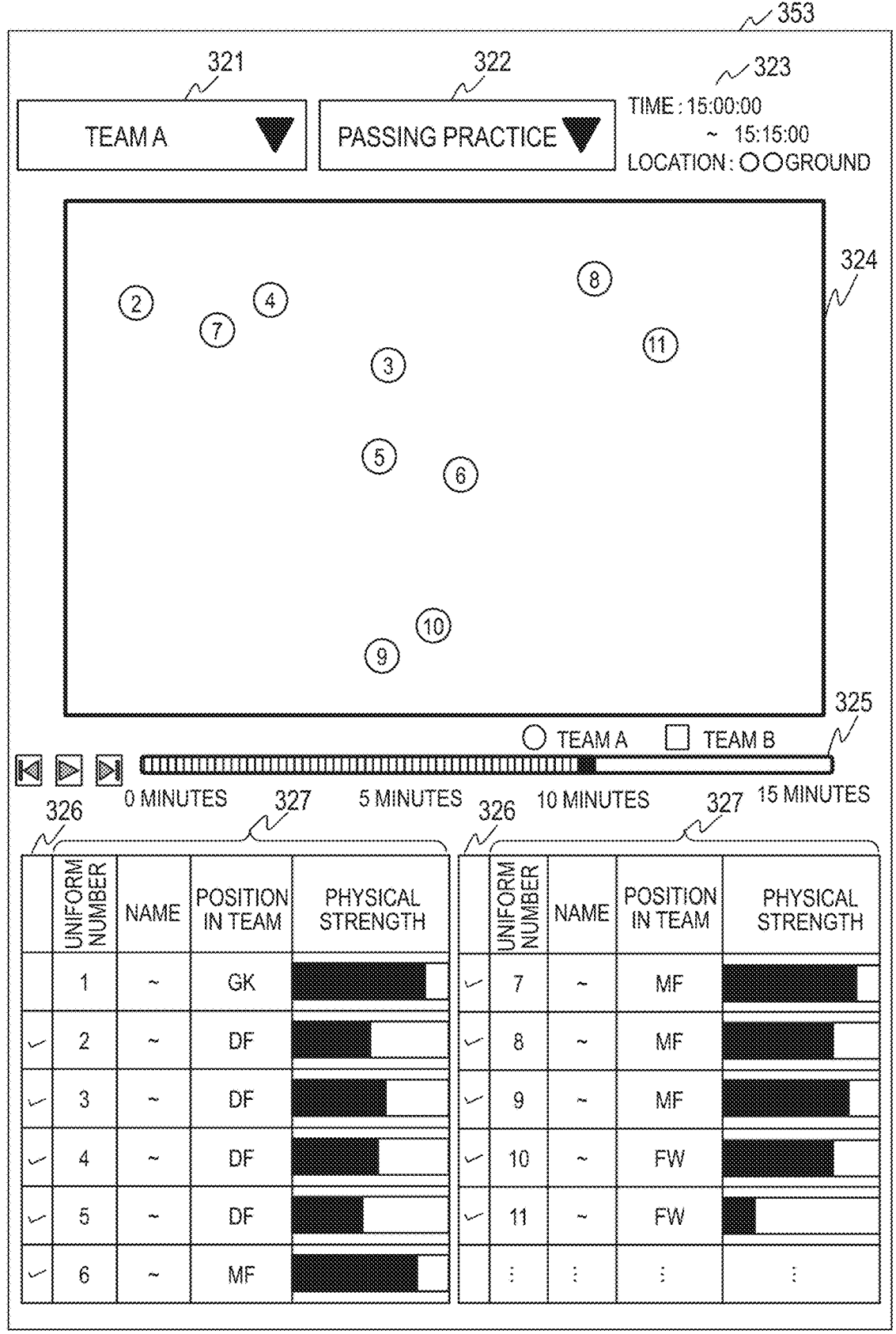
FIG. 20 is an explanatory diagram for showing the screen generated by the display module according to the second embodiment.

FIG. 20 is an explanatory diagram for showing the screen 353 generated by the display module 13 according to the second embodiment.

The screen 353 is for showing a result of track monitoring of participants at soccer practice. The individual identification module 11 and the track generation module 12 are configured to generate tracks and movements of the individuals for each practice menu based on track information and sensor data identified by referring to the environment information 27. The display module 13 is configured to display information indicating the tracks of the participants at soccer practice on the screen 353.

The screen 353 includes images 321, 322, 323, 324, 325, and 326. The image 321 displays an interface that allows the operator to select the team name. The image 322 displays an interface that allows the operator to select the activity name of the athletic activity. In FIG. 20, the athletic activity is soccer, and the activity name shows the soccer practice content.

The image 323 displays the time (corresponding to the start time point 2072 and the finish time point 2073) and the location (corresponding to the area name 2012 identified based on the area ID 2074) at which the content of the athletic activity selected in the image 322 was performed. The image 324 displays the tracks of the participants on the field (based on the individual track information 26). The numerals in the image 324 indicate the uniform numbers of the participants (based on the user type 2043 in the user information table 204).

The analysis module 10 may also be configured to execute, when the team name and the activity name have been input in the images 321 and 322, the processing illustrated in FIG. 19 based on the activity ID of the input activity name. Further, the display module 13 may also be configured to display the image 324 based on a result of the processing illustrated in FIG. 19.

Further, the display module 13 is configured to identify the users 30 on which track information is to be displayed based on the activity ID of the input activity name and the team name. Specifically, the activity ID of the input activity name is identified based on the activity information table 206. In addition, an entry in the environment information table 270 including the identified activity ID in the activity ID 2071 is identified, and from the user ID 2075 of the identified entry, the users 30 belonging to the team having the input team name are identified based on the user type 2043 in the user information table 204. Still further, the tracks are displayed in the image 324 by using the individual track information 26 of the identified users 30 (the individual track information 26 in the input activity name).

In addition, the image 325 shows a timeline of the measurement date and time. The operator inputs the positions and tracks for an arbitrary measurement date and time by operating the timeline in the image 325. The display module 13 is configured to display the tracks in the image 324 in the form of an animated graphic, for example, based on the individual track information 26.

The user type 2043 in the user information table 204 stores information on the users 30 (information such as, but not limited to, grouping during practice, uniform number, position in team, etc.), and hence the display module 13 can display in an image 327 information on the users 30 of each team.

Further, when the sensor data 22 includes a result obtained by measuring an arm movement amount, as in the first embodiment, a remaining physical strength can be estimated for each measurement date and time. Therefore, the remaining physical strength during the match may be displayed in the image 327 for the measurement date and time specified by the timeline in the image 325.

The display module 13 may be configured to change, when the users 30 have been selected by the operator in the image 326, the users 30 for which a track is to be displayed in the image 324.

The use by the analysis module 10 of the environment information 27 enables individual track information to be displayed even when practice is performed at a different location or when the members are replaced for each practice menu. As a result, the analysis system according to the embodiment can be utilized in daily training.

FIG. 21 is an explanatory diagram for showing a screen 354 generated based on the speed information 23 according to the first embodiment.

The screen 354 is a screen for showing an analysis result of the performance of the participants (users 30) in soccer practice. The display module 13 is configured to display on the screen 354 the performance of the participating players in each practice menu based on track information and sensor data extracted by referring to the environment information 27 and the individual track information 26. The screen 354 includes images 328, 329, 330, 331, and 332.

The operator selects the team name for which he or she wishes a performance analysis result to be displayed by using a tab in the image 328, and a practice menu (activity name) for which he or she wishes an analysis result to be displayed in the image 329. The image 330 displays the time and the location at which the practice menu selected in the image 329 was performed.

The image 331 displays various types of information, such as, but not limited to, the distance traveled, the top speed, and the number of sprints, during the practice selected in the image 329. The image 332 displays the respective proportions of standing still, walking, jogging, sprinting, and dribbling of each user 30, which is calculated based on the speed information 23.

FIG. 22 is an explanatory diagram for showing a screen 355 for displaying an analysis result of the performance of one user 30 according to the second embodiment.

The screen 355 is for displaying an analysis result of the performance of one player (user 30) in soccer practice, and is generated by the display module 13. The display module 13 is configured to display on the screen 355 the individual performance in each practice menu based on track information and sensor data extracted by referring to the environment information 27, for example. The screen 355 includes images 333, 334, 335, and 336.

The operator selects a player name that he or she wishes to refer by using a tab in the image 333. The image 334 displays various types of information, such as, but not limited to, the distance traveled, the top speed, and the number of sprints, of each practice menu.

The image 335 displays the respective proportions of standing still, walking, jogging, and sprinting of each practice menu. Further, the image 336 displays in a radar chart various types of information, such as, but not limited to, the distance traveled and the top speed, for the menu selected in an image 337. As a result, the operator can compare the performance of each practice menu.

Third Embodiment

Track monitoring in the child care and educational fields according to a third embodiment of this invention is now described with reference to the drawings. The analysis module 10 according to the third embodiment is configured to detect the tracks and movements of the users 30 by using group track information 21 in the child care and educational fields, and sensor data 22 from wearable devices 2. As a result, play and communication can be evaluated, and a visualization of group living can be realized.

The track monitoring system according to the third embodiment is the same as the track monitoring system according to the first embodiment and the second embodiment.

Figure 23:
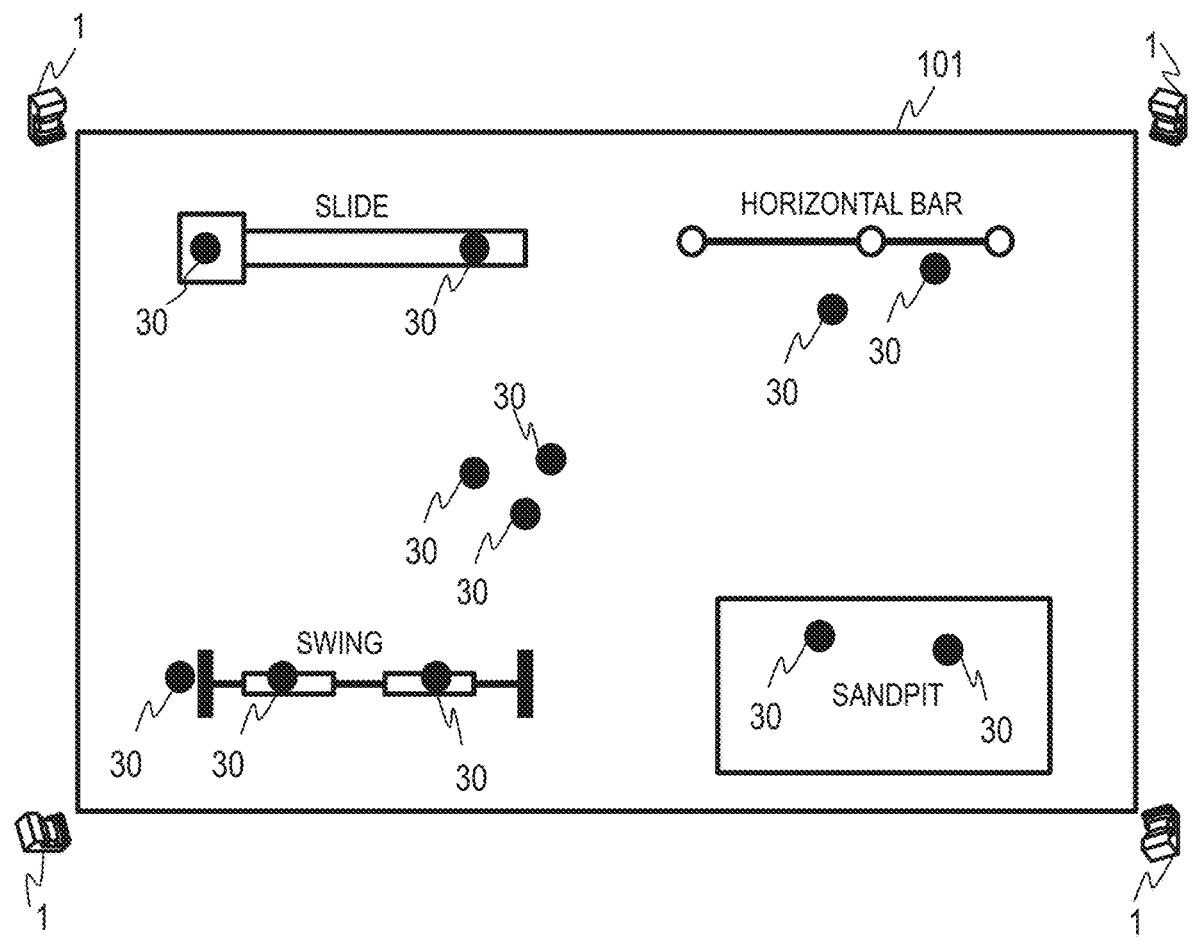
FIG. 23 is an explanatory diagram for illustrating subjects of track monitoring in the child care field according to the third embodiment.

FIG. 23 is an explanatory diagram for illustrating subjects of track monitoring in the child care field according to the third embodiment.

A laser radar in the position detection apparatus 1 illustrated in FIG. 23 is arranged at a position capable of detecting the position of an object by reflection of laser light. One or more laser radars are arranged at positions capable of measuring the whole area of a ground 101 in a children's facility (a nursery school or a kindergarten).

It is desired that the position detection apparatus 1 be arranged at a position at which the radiated laser light and the plane of the field are horizontal. On the other hand, because the position coordinates may be corrected by the position detection apparatus 1 and the PC 3, the position detection apparatus 1 may be arranged in various locations without restriction, such as locations that are sloped.

The position detection apparatus 1 is not limited to being arranged on a ground 101, and the position detection apparatus 1 may be arranged in an indoor hall, a corridor, and the like. Further, other than laser light, the position detection apparatus 1 may be configured to measure position by using a method employing video analysis to measure the position of an object. This invention is not limited to the above-mentioned position detection apparatus 1 that uses laser light or video analysis, and any position detection apparatus 1 may be used as long as the apparatus is capable of measuring position.

One or more wearable devices 2 are worn on the body of each user 30 (child) who is playing on the ground 101. Each child in the third embodiment wears directly on his or her wrist a wristwatch-type wearable device 2 including a triaxial acceleration sensor.

In the example described above, each user 30 is wearing directly on his or her wrist a wristwatch-type wearable device 2. However, the wearable device 2 includes at least one or more sensors selected from among various sensors.

The sensors included in the wearable device 2 in the childcare field according to the third embodiment are the same as for the wearable device 2 according to the first embodiment. Any sensor may be included, and, the wearable device 2 may be worn on any site of the user 30.

Figure 24:
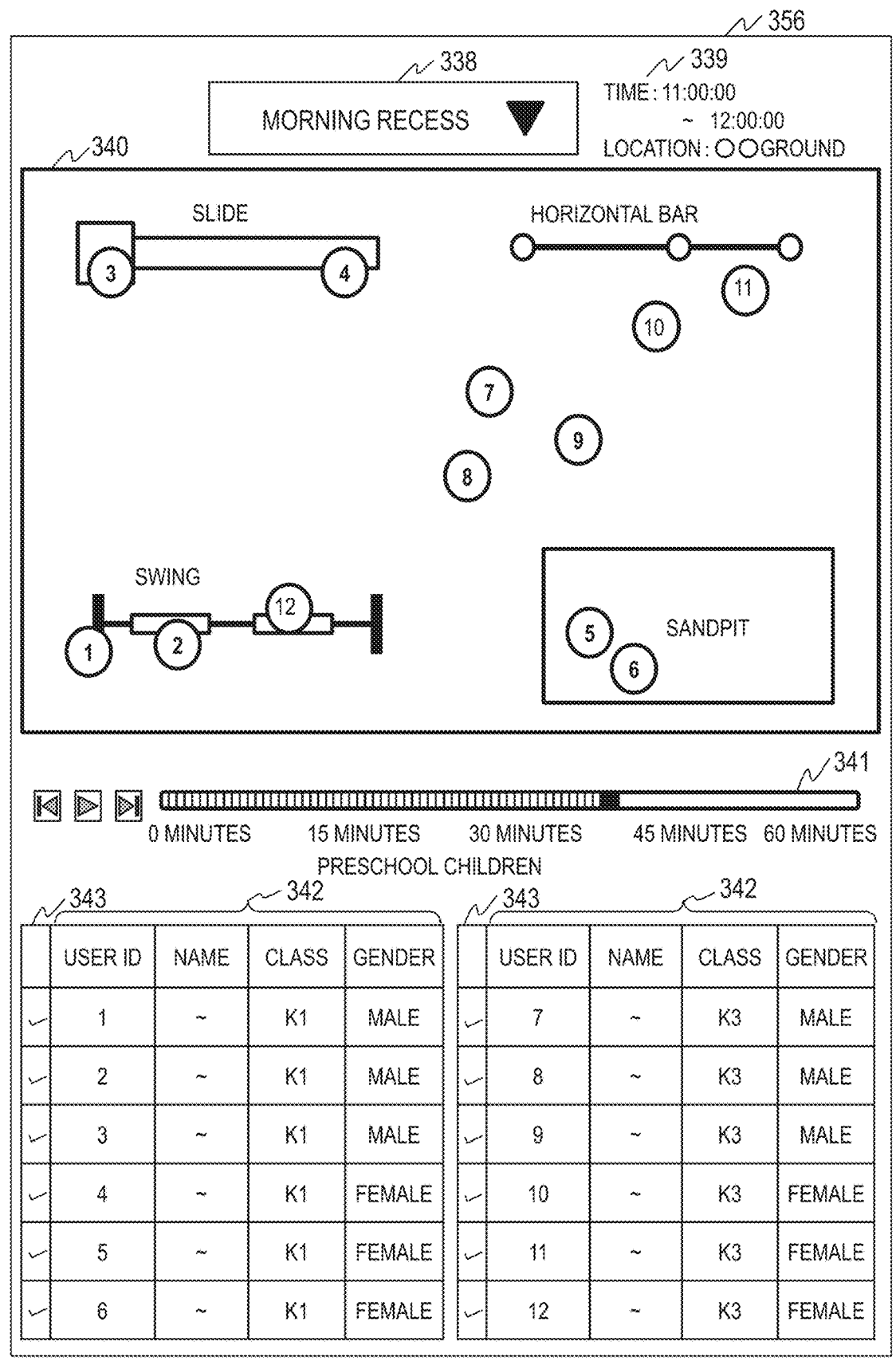
FIG. 24 is an explanatory diagram for showing a screen in the childcare field according to the third embodiment.

FIG. 24 is an explanatory diagram for showing a screen 356 in the childcare field according to the third embodiment.

The screen 356 is for showing a result obtained by monitoring tracks, in which children's play is the athletic activity. Further, the display module 13 according to the third embodiment is configured to generate the tracks and movements of the children for each active time specified in advance, by using, as in the second embodiment, track information extracted by referring to environment information 27 and others. The display module 13 according to the third embodiment may also be configured to display the track information on the children for each activity.

The screen 356 includes images 338, 339, 340, 341, 342, and 343.

The operator may select the athletic activity to be referred to by using a tab on the image 338. The image 339 may display the time and location at which the track was measured, or may display the time and location at which the selected athletic activity was performed.

The image 340 displays the track of each child (user 30) on the ground 101. The numerals displayed in the image 340 indicate user IDs. The operator displays the tracks for an arbitrary measurement date and time by operating the timeline in the image 341.

The display module 13 is configured to display, when the user type 2043 in the user information table 204 stores various types of information, such as, but not limited to, the class, gender, and the like of the child, those pieces of information in the image 342. The operator selects the child for which a track is to be displayed in the image 340 by selecting the child (user 30) in the image 343.

Further, including an infrared sensor and an audio sensor in the wearable device 2 enables an interaction count and a conversation count between children to be measured simultaneously with the track information. This information may be displayed in addition to the track information.

Arranging the position detection apparatus 1 in locations other than the ground 101, such as in an indoor classroom or corridor, enables the tracks of the children to be monitored in any part of the children's facility. As a result, how the athletic activities by the children are performed can be monitored based on the third embodiment, and the frequency of communication by each individual, group formation processes, and the like can be measured.

Figure 25:
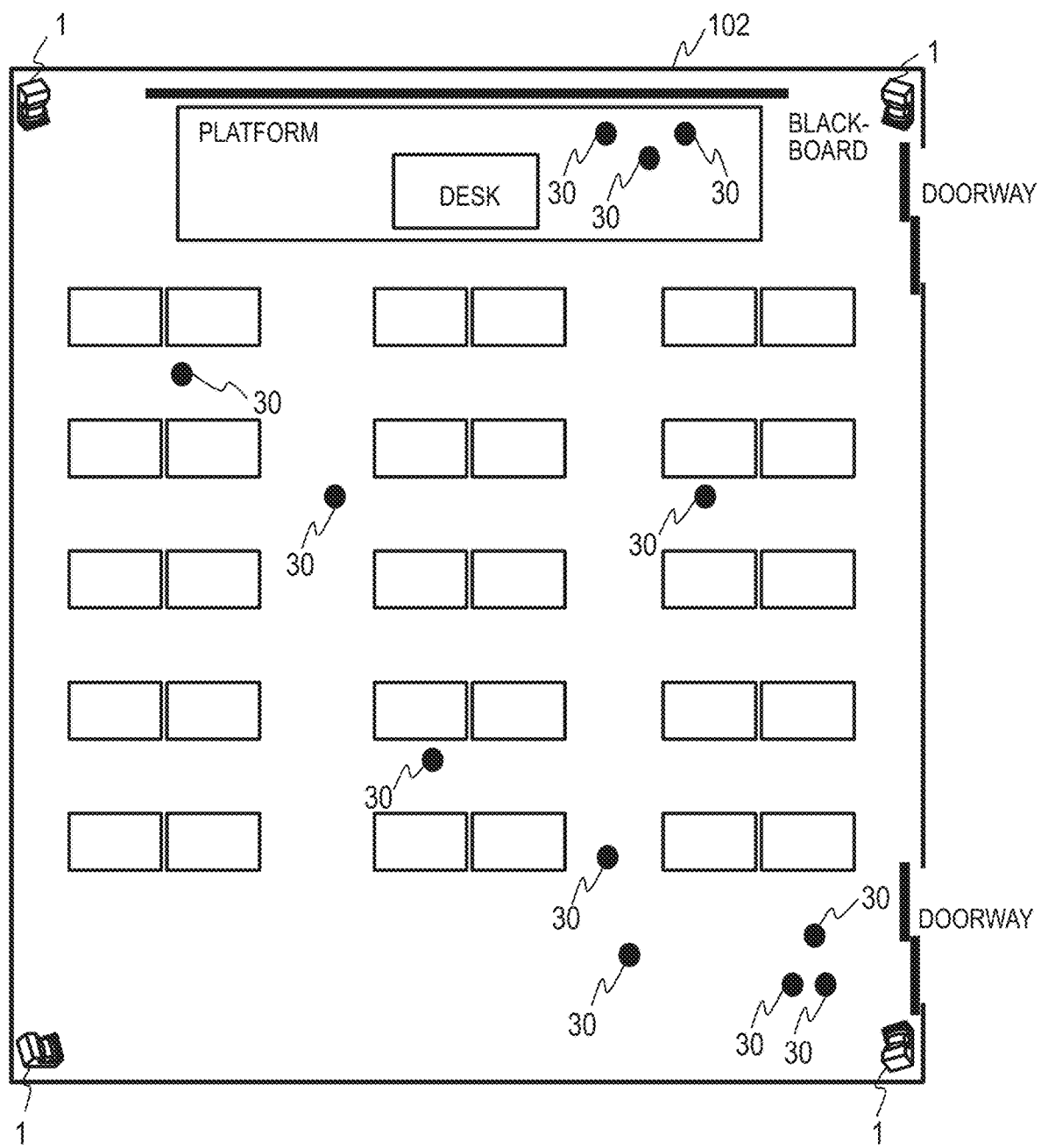
FIG. 25 is an explanatory diagram for illustrating subjects of track monitoring in the educational field according to the third embodiment.

FIG. 25 is an explanatory diagram for illustrating subjects of track monitoring in the educational field according to the third embodiment.

A laser radar in the position detection apparatus 1 illustrated in FIG. 25 is arranged at a position capable of detecting the position of an object by reflection of laser light. One or more laser radars are arranged at positions capable of measuring the whole area of a classroom 102 in a school.

It is desired that the position detection apparatus 1 be arranged at a position at which the radiated laser light and the horizontal plane of the classroom 102 are parallel. On the other hand, because the position coordinates may be corrected by the position detection apparatus 1 and the PC 3, the position detection apparatus 1 may be arranged in various locations without restriction, such as on the ceiling of the classroom 102.

The position detection apparatus 1 is not limited to being arranged on a classroom 102, and the position detection apparatus 1 may be arranged in a corridor, a ground, a cafeteria, and the like. Other than laser light, the position detection apparatus 1 may be configured to measure position by using a method employing video analysis to measure the position of an object. This invention is not limited to the above-mentioned position detection apparatus 1 that uses laser light or video analysis, and any position detection apparatus 1 may be used as long as the apparatus is capable of measuring position.

One or more wearable devices 2 are worn on the body of each user 30 (school child) who is moving in the classroom 102. Each school child in the third embodiment wears directly on his or her wrist a wristwatch-type wearable device 2 including a triaxial acceleration sensor.

The sensors included in the wearable device 2 in the educational field according to the third embodiment are the same as for the wearable device 2 according to the first embodiment. Any sensor may be included, and, the wearable device 2 may be worn on any site of the user 30.

Figure 26:
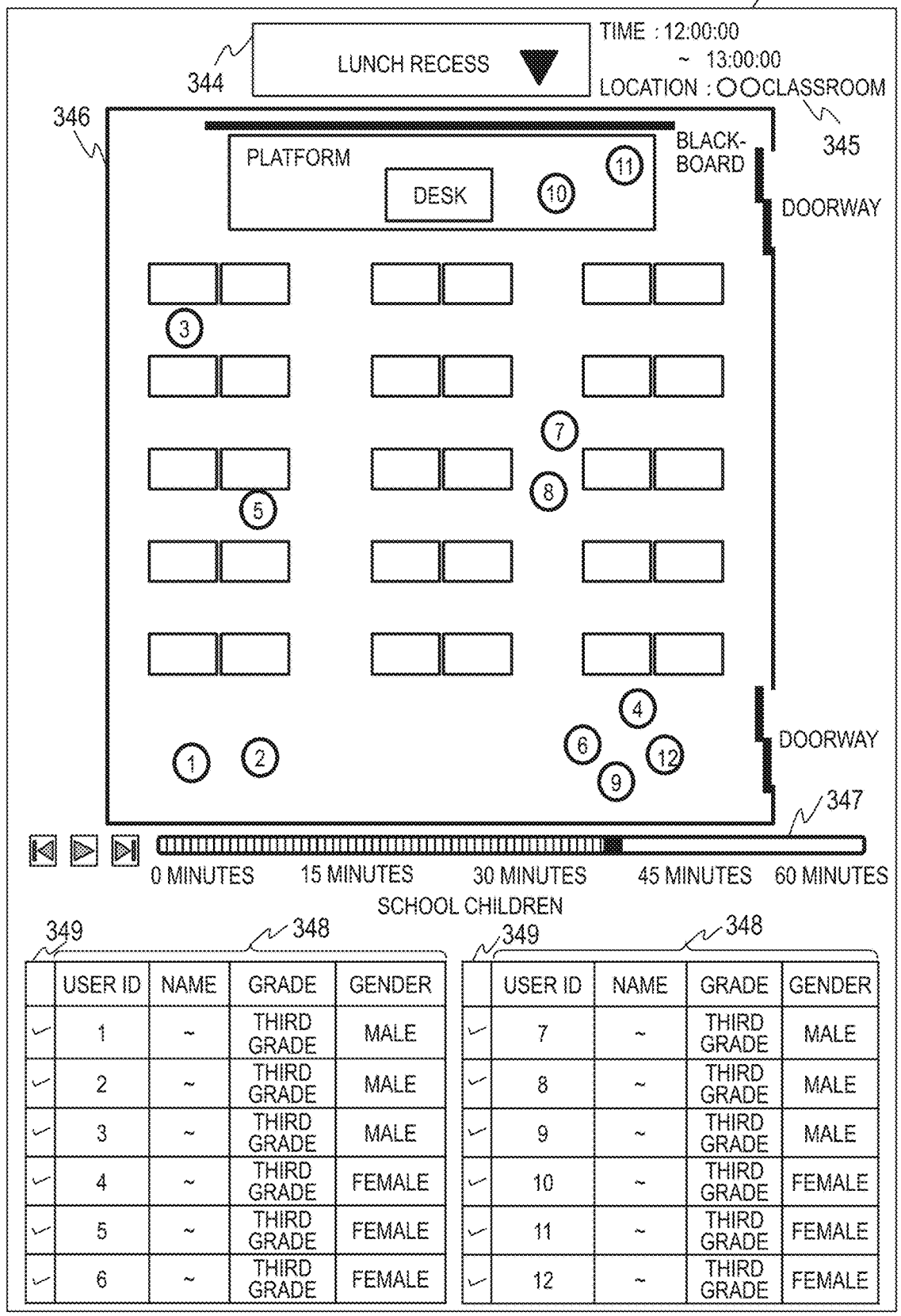
FIG. 26 is an explanatory diagram for showing a screen in the educational field according to the third embodiment.

FIG. 26 is an explanatory diagram for showing a screen 357 in the educational field according to the third embodiment.

The screen 357 is for showing a result obtained by monitoring tracks, in which school children's movement in the classroom is the athletic activity. The display module 13 according to the third embodiment is configured to generate the tracks and movements of the school children for each active time specified in advance, by using, as in the second embodiment, track information extracted by referring to environment information 27 and others. The display module 13 according to the third embodiment may also be configured to display the track information on the school children for each activity.

The screen 357 includes images 344, 345, 346, 347, 348, and 349.

The operator may select the athletic activity to be referred to by using a tab on the image 344. The image 345 may display the time and location at which the track was measured, or may display the time and location at which the selected athletic activity was performed.

The image 346 displays the track of each school child (user 30) in the classroom 102. The numerals displayed in the image 346 indicate user IDs. The operator displays the tracks for an arbitrary measurement date and time by operating the timeline in the image 347.

The display module 13 is configured to display, when the user type 2043 in the user information table 204 stores various types of information, such as, but not limited to, the class, gender, and the like of the school child, those pieces of information in the image 348. The operator selects the school child for which a track is to be displayed in the image 346 by selecting the school child in the image 349.

Further, including an infrared sensor and an audio sensor in the wearable device 2 enables an interaction count and a conversation count between school children to be measured simultaneously with the track information. This information may be displayed in addition to the track information.

Arranging the position detection apparatus 1 in locations other than the classroom 102, such as in a corridor, cafeteria, or ground, enables the tracks of the school children to be monitored in any part of the school. As a result, how the athletic activities by the school children are performed can be monitored based on the third embodiment, and the frequency of communication by each individual, group formation processes, and the like can be measured.

Although the present disclosure has been described with reference to exemplary embodiments, those skilled in the art will recognize that various changes and modifications may be made in form and detail without departing from the spirit and scope of the claimed subject matter.

The present invention is not limited to the above-described embodiments but includes various modifications. The above-described embodiments are explained in details for better understanding of this invention and are not limited to those including all the configurations described above. A part of the configuration of one embodiment may be replaced with that of another embodiment; the configuration of one embodiment may be incorporated to the configuration of another embodiment. A part of the configuration of each embodiment may be added, deleted, or replaced by that of a different configuration.

The above-described configurations, functions, and processors, for all or a part of them, may be implemented by hardware: for example, by designing an integrated circuit. The above-described configurations and functions may be implemented by software, which means that a processor interprets and executes programs providing the functions. The information of programs, tables, and files to implement the functions may be stored in a storage device such as a memory, a hard disk drive, or an SSD, or a storage medium such as an IC card, or an SD card.

The drawings shows control lines and information lines as considered necessary for explanations but do not show all control lines or information lines in the products. It can be considered that almost of all components are actually interconnected.

What is claimed is:

1. An analysis system, comprising: a position detection apparatus including a laser irradiation module for use in determining a position of an individual; a wearable device, including an acceleration sensor, that is worn by the individual; a smartphone configured to communicate with the wearable device via a network; and a server including: a storage module configured to store a track indicating in a time series the position of the individual that is moving as track data, and store sensor data indicating in the time series a measurement result of the individual by the acceleration sensor worn by the individual; and an analysis module programmed to: calculate a speed index indicating a movement speed of the individual based on the track data; calculate a behavior index indicating a movement intensity of the individual based on the sensor data; calculate a degree of similarity between the speed index and the behavior index based on changes in the time series of the speed index and the behavior index; and associate the track and the individual on which the sensor data has been measured based on the degree of similarity.

2. The analysis system according to claim 1, further comprising an input module configured to receive identification information comprising identification information for identifying the track and information for identifying an individual on which the sensor data has been measured, wherein the analysis module is configured to calculate a speed index indicating a speed on the track identified based on the identification information,
calculate a behavior index of the individual identified based on the identification information,
calculate a degree of similarity between the speed index of the track and the behavior index of the individual, and
associate the track and the individual on which the sensor data has been measured based on the degree of similarity between the speed index of the track and the behavior index of the individual.

3. The analysis system according to claim 1, wherein the track includes a plurality of tracks and the analysis module is configured to calculate, when the plurality of tracks and the individual have been associated with each other, distances among the plurality of tracks to determine whether or not the plurality of tracks associated with the individual are suitable based on the distances, and
change the individual to be associated with at least one of the plurality of tracks when it is determined that the plurality of tracks associated with the individual are not suitable.

4. The analysis system according to claim 3,
wherein the analysis module is configured to associate a first track and a second track of the plurality of tracks with the individual,
determine that the first track and the second track associated with the individual are not suitable when a distance between the first track and the second track is equal to or more than a predetermined threshold, and
identify, when it is determined that the first track and the second track associated with the first individual are not suitable, a second individual calculated as having a degree of similarity with the first track that is lower than the degree of similarity between the speed index based on the first track and the behavior index of the first individual, and change the individual to be associated with the first track to the second individual.

5. The analysis system according to claim 1,
wherein the analysis module is configured to:
calculate a plurality of first degrees of similarity between a speed index based on the track detected for a longest period of time and a plurality of behavior indices; and
calculate, when the plurality of first degrees of similarity are included in a predetermined range, a plurality of second degrees of similarity between a speed index based on the track detected for a second longest period of time and the plurality of behavior indices, and
wherein the analysis module is configured to associate the track detected for the second longest period of time and the individual on which the sensor data has been measured based on the plurality of second degrees of similarity.

6. The analysis system according to claim 1, wherein the analysis module is configured to associate the track and information indicating the individual associated with the track to generate screen data to be displayed in the time series.

7. The analysis system according to claim 1, wherein the movement intensity is expressed as a number of metabolic equivalents (METs).

8. An analysis method to be performed in an analysis system that includes a position detection apparatus including a laser irradiation module for use in determining a position of an individual; a wearable device, including an acceleration sensor, that is worn by the individual; a smartphone that communicates with the wearable device via a network; and a server including a storage module configured to store a track indicating in a time series the position of the individual that is moving as track data and store sensor data indicating in the time series a measurement result of the individual by the acceleration sensor worn by the individual, and an analysis module programmed to execute the analysis method, comprising: irradiating the individual with light from the laser irradiation module to determine the position of the individual; receiving the measurement result from the acceleration sensor of the wearable device; storing the track indicating in the time series the position of the individual that is moving as the track data in the storage module, and storing the sensor data indicating in the time series the measurement result of the individual by the acceleration sensor worn by the individual in the storage module; calculating, by the analysis module, a speed index indicating a movement speed of the individual based on the track data; calculating, by the analysis module, a behavior index indicating a movement intensity of the individual based on the sensor data; calculating, by the analysis module, a degree of similarity between the speed index and the behavior index based on changes in the time series of the speed index and the behavior index; and associating, by the analysis module, the track and the individual on which the sensor data has been measured based on the degree of similarity.

9. The analysis method according to claim 8, further comprising receiving, by the analysis module, as an input, identification information comprising identification information for identifying the track and information for identifying an individual on which the sensor data has been measured,
wherein the calculating of the speed index comprises calculating a speed index indicating a speed on the track identified based on the identification information,
wherein the calculating of the behavior index comprises calculating a behavior index of the individual identified based on the identification information,
wherein the calculating of the degree of similarity comprises calculating a degree of similarity between the speed index of the track and the behavior index of the individual, and
wherein the associating of the track and the individual comprises associating the track and the individual on which the sensor data has been measured based on the degree of similarity between the speed index of the track and the behavior index of the individual.

10. The analysis method according to claim 8, wherein when the track includes a plurality of tracks, further comprising calculating, by the analysis module, when the plurality of tracks and the individual have been associated, distances among the plurality of tracks to determine whether or not the plurality of tracks associated with the individual are suitable based on the distances,
wherein the associating of the track and the individual comprises changing the individual to be associated with at least one of the plurality of tracks when it is determined in the determining of the plurality of tracks that the plurality of tracks associated with the individual are not suitable.

11. The analysis method according to claim 10,
wherein the associating of the track and the individual comprises associating a first track and a second track of the plurality of tracks with the individual,
wherein the determining of the plurality of tracks comprises determining that the first track and the second track associated with the first individual are not suitable when a distance between the first track and the second track is equal to or more than a predetermined threshold, and
wherein the associating of the track and the individual comprises identifying, when it is determined that the first track and the second track associated with the individual are not suitable, a second individual that has a degree of similarity with the first track that is lower than the degree of similarity between a speed index of the first track and the behavior index of the individual, and changing the individual to be associated with the first track to the second individual.

12. The analysis method according to claim 8,
wherein the calculating of the degree of similarity comprises:
calculating a plurality of first degrees of similarity between a speed index based on the track detected for a longest period of time and a plurality of behavior indices; and
calculating, when the plurality of first degrees of similarity are included in a predetermined range, a plurality of second degrees of similarity between a speed index based on the track detected for a second longest period of time and the plurality of behavior indices, and
wherein the associating of the track and the individual comprises associating the track detected for the second longest period of time and the individual on which the sensor data has been measured based on the plurality of second degrees of similarity.

13. The analysis method according to claim 8, further comprising associating, by the analysis module, the track and information indicating the individual associated with the track to generate screen data to be displayed in the time series.

14. The analysis method according to claim 8, wherein the movement intensity is expressed as a number of metabolic equivalents (METs).

* * * * *